(12) United States Patent
Martini et al.

(10) Patent No.: US 7,961,326 B2
(45) Date of Patent: Jun. 14, 2011

(54) METHOD OF DETECTING THE CONCENTRATION OF AN ANALYTE

(75) Inventors: Joerg Martini, San Francisco, CA (US); Richard H. Bruce, Los Altos, CA (US); Francisco E. Torres, San Jose, CA (US); Peter Kiesel, Palo Alto, CA (US); Michael I. Recht, Mountain View, CA (US); Jeffrey N. Roe, San Ramon, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 328 days.

(21) Appl. No.: 12/195,997

(22) Filed: Aug. 21, 2008

(65) Prior Publication Data
US 2010/0045993 A1 Feb. 25, 2010

(51) Int. Cl.
*A61B 5/00* (2006.01)
*G01J 3/46* (2006.01)
(52) U.S. Cl. ............ 356/433; 356/448; 356/39; 600/316
(58) Field of Classification Search .............. 356/39–42, 356/433, 436, 440–442; 600/160–182
See application file for complete search history.

(56) References Cited

U.S. PATENT DOCUMENTS

| 4,448,534 A * | 5/1984 | Wertz et al. ................ 356/435 |
| 5,560,356 A | 10/1996 | Peyman |
| 6,256,522 B1 * | 7/2001 | Schultz ..................... 600/317 |
| 6,952,603 B2 | 10/2005 | Gerber |
| 7,016,714 B2 * | 3/2006 | Colvin, Jr. .................. 600/316 |
| 7,043,289 B2 | 5/2006 | Fine |
| 7,135,342 B2 * | 11/2006 | Colvin et al. ................ 436/164 |

(Continued)

FOREIGN PATENT DOCUMENTS

EP 1953532 A2 8/2008

(Continued)

OTHER PUBLICATIONS

European Search Report, EP Application No. 09167956.3-1265, Dated Dec. 1, 2009, The Hague.

(Continued)

*Primary Examiner* — Gregory J Toatley
*Assistant Examiner* — Rebecca C Slomski
(74) *Attorney, Agent, or Firm* — Fay Sharpe LLP

(57) ABSTRACT

A system and method is provided for detecting concentration of an analyte in a fluid. The method comprises detecting an optical property of a first region of two or more regions in a system, the first region located in a container having a reservoir for one or more modifiers of one or more optical properties of the first region. The movement of the one or more modifiers is responsive to changes in concentration of the analyte. A next step detects an optical property of a second region of the two or more regions in the system, the second region located in a container having a reservoir for one or more modifiers of one or more optical properties of the second region. The movement of the one or more modifiers is responsive to changes in concentration of a compound, where the compound is something other than the analyte. The detected optical property of the first region and the detected optical property of the second region are used in embodiments to separate the effect of the analyte on the detected optical property of the first region from the effect of the compound, where the compound is an interfering compound.

34 Claims, 9 Drawing Sheets

U.S. PATENT DOCUMENTS

| | | | |
|---|---|---|---|
| 7,226,414 | B2 | 6/2007 | Ballerstadt |
| 7,236,812 | B1 | 6/2007 | Ballerstadt |
| 7,254,429 | B2 | 8/2007 | Schurman |
| 7,291,824 | B2 | 11/2007 | Kiesel |
| 7,358,476 | B2 | 4/2008 | Kiesel |
| 2004/0072358 | A1 | 4/2004 | Ballerstadt et al. |
| 2007/0148760 | A1 | 6/2007 | Kiesel |
| 2008/0021293 | A1 | 1/2008 | Schurman |
| 2008/0186483 | A1 | 8/2008 | Kiesel |
| 2008/0186492 | A1 | 8/2008 | Kiesel |
| 2008/0186494 | A1 | 8/2008 | Kiesel |
| 2008/0186500 | A1 | 8/2008 | Schmidt |
| 2008/0186503 | A1 | 8/2008 | Kiesel |

FOREIGN PATENT DOCUMENTS

| | | | |
|---|---|---|---|
| EP | | 1953535 A2 | 8/2008 |

OTHER PUBLICATIONS

European Search Report, EP Application No. 09167957.2-1265, Dated Dec. 1, 2009, The Hague.

B. B. Agrawal and I. J. Goldstein. "Specific binding of concanavalin A to cross-linked dextran gels", *Biochemical Journal* 96(3), 23c-25c (1965).

R. Russell, M. Pishko, C. Gefrides and G. Cote. "A fluorescent glucose assay using poly-L-lysine and calcium alginate microencapsulated TRITC-succinyl-concanavalin A and FITC-dextran", Pishko, M. 20, 2858-2861 (1998) *Engineering in Medicine and Biology Society*, 1998. Proceedings of the 20th Annual International Conference of the IEEE. Gefrides, C.

R. Ballerstadt and J. S. Schultz. "A fluorescence affinity hollow fiber sensor for continous transdermal glucose monitoring", *Anal.Chem.* 72(17), 4185-4192 (2000).

U.S. Appl. No. 11/957,610, filed Dec. 17, 2007, Martini.

R. Ballerstadt, A. Kholodnykh, C. Evans, A. Boretsky, M. Motamedi, A. Gowda and R. McNichols. "Affinity-based turbidity sensor for glucose monitoring by optical coherence tomography: toward the development of an implantable sensor", *Anal.Chem.* 79(18), 6965-6974 (2007).

S. Goto, K. Masuda, M. Miura, K. Kanazawa, M. Sasaki, M. Masui, M. Shiramizu, H. Terada and H. Chuman. "Quantitative estimation of interaction between carbohydrates and concanavalin A by surface plasmon resonance biosensor", *Chem.Pharm.Bull.*(Tokyo). 50(4), 445-449 (2002).

R. Ballerstadt and J. S. Schultz. "Kinetics of dissolution of Concanavalin A/Dextran sols in response to glucose measured by surface plasmon resonance", *Sensors and Actuators B: Chemical* 46(1), 50-55 (1998).

O. S. Khalil. "Spectroscopic and clinical aspects of noninvasive glucose measurements", *Clin. Chem.* 45(2), 165-177 (1999).

J. L. Wang and G. M. Edelman. "Binding and functional properties of concanavalin A and its derivatives. I. Monovalent, divalent, and tetravalent derivatives stable at physiological pH", *J.Biol.Chem.* 253(9), 3000-3007 (1978).

R. Ballerstadt, C. Evans, A. Gowda and R. McNichols. "In vivo performance evaluation of a transdermal near-infrared fluorescence resonance energy transfer affinity sensor for continuous glucose monitoring", *Diabetes Technol.Ther.* 8(3), 296-311 (2006).

R. Ballerstadt, A. Gowda and R. McNichols. "Fluorescence resonance energy transfer-based near-infrared fluorescence sensor for glucose monitoring", *Diabetes Technot.Ther.* 6(2), 191-200 (2004).

J. J. Kim and K. Park. "Glucose-binding property of pegylated concanavalin A", *Pharm.Res.* 18(6), 794-799 (2001).

\* cited by examiner

METHOD OF DETECTING THE CONCENTRATION OF AN ANALYTE

BACKGROUND

The present application relates generally to techniques involving production and use of articles and systems, such as to obtain information about analytes in fluids. More specifically it is directed to techniques which can provide specificity in measurements of concentration of a target analyte, such as glucose, in bodily fluids, including techniques involving production and use of implantable articles and systems.

Various implantable devices have been proposed. For example, implantable devices for monitoring glucose that are based on electrochemical sensors and glucose oxidase enzymatic reaction are available. These devices have the disadvantages that they produce the cytotoxic byproduct $H_2O_2$, they require the glucose oxidase to remain active, and they require electrical current to complete the electrochemical circuit. It would be desirable to have a device that does not have these disadvantages.

Another example of an implantable device is given in U.S. Pat. No. 6,952,603, which describes an implantable optical sensing element with a body and with a membrane mounted on the body, defining a cavity. This device is based on physical sensing rather than electrochemical sensing. The membrane is permeable to an analyte while impermeable to background species. A refractive index (RI) element is positioned in the cavity. A light source transmits light of a first intensity onto the refractive element, and a light detector receives light of a second intensity that is reflected/transmitted from/through the cavity. A controller device coupled to the detector compares the first and second light intensities and relates them to the refractive index, which in turn is related to analyte concentration. For the device to function properly, the membrane needs to be impermeable to background species because those species can alter the refractive index. Although filters can readily prevent passage of some background compounds, there are others that are more difficult to block. For example, it would be difficult to design a filter to block small uncharged molecules with molecular weight between about 50 and 500 Da while letting an analyte of similar size, e.g. glucose, through. It would be desirable to have a non-electrochemical device that has improved specificity for the analyte of interest.

More generally, it would be advantageous to have improved techniques for implantable articles and systems, including improved techniques for providing specificity for a target analyte.

INCORPORATION BY REFERENCE

This application is related to the following co-pending applications, each of which is hereby incorporated by reference in its entirety: "Improved Specificity Of Analyte Detection In Etalons", U.S. Pat. No. [Unknown], filed herewith, by Joerg Martini et al.; "Sensing Photons from Objects in Channels", U.S. patent application Ser. No. 11/315,992, now published as U.S. Patent Publication No. 2007/0145249; "Obtaining Analyte Information", U.S. patent application Ser. No. 11/316,303, now published as U.S. Patent Publication No. 2007/0148760; "Obtaining Information From Optical Cavity Output Light", U.S. patent application Ser. No. 11/702,249; "Photosensing Optical Cavity Output Light", U.S. patent application Ser. No. 11/702,250; "Containing Analyte In Optical Cavity Structures", U.S. patent application Ser. No. 11/702,325; "Implanting Optical Cavity Structures", U.S. patent application Ser. No. 11/702,329; "Encoding Optical Cavity Output Light", U.S. patent application Ser. No. 11/702,363; and "Controlling Transfer of Objects Affecting Optical Characteristics", U.S. patent application Ser. No. 11/957,610.

BRIEF DESCRIPTION

A system and method is provided for detecting concentration of an analyte in a fluid. The method comprises detecting an optical property of a first region of two or more regions in a system, the first region located in a container having a reservoir for one or more modifiers of one or more optical properties of the first region. The movement of the one or more modifiers is responsive to changes in concentration of the analyte. A next step detects an optical property of a second region of the two or more regions in the system, the second region located in a container having a reservoir for one or more modifiers of one or more optical properties of the second region. The movement of the one or more modifiers is responsive to changes in concentration of a compound, where the compound is something other than the analyte. The detected optical property of the first region and the detected optical property of the second region are used in embodiments to separate the effect of the analyte on the detected optical property of the first region from the effect of the compound, where the compound is an interfering compound.

DETAILED DESCRIPTION

Figure 1:
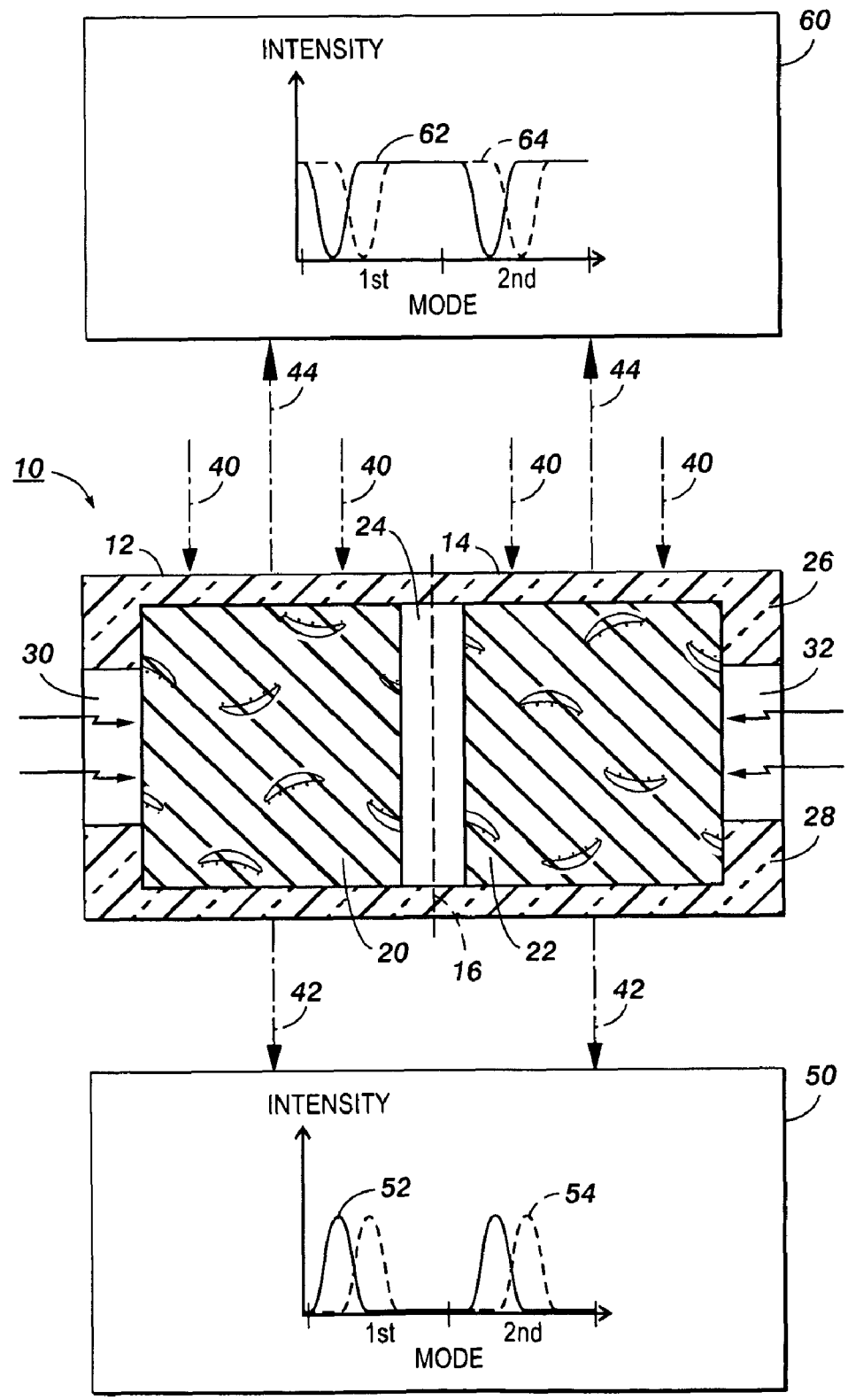
FIG. 1 is a schematic diagram showing optical and fluidic operations of an article that can be implanted in a body.

Turning now more particularly to the details of the present application, the following description initially provides an overview of the concepts of the present application. In the overview, an exemplary system employing some concepts of the present application is provided. Thereafter, a system setting the environment in which the present concepts may be employed is provided. Thereafter, a more detailed discussion of systems and methods employing concepts of the present application is set out.

I. Overview

A system of the present application detects the concentration of an analyte in a fluid by measuring change in one or more optical properties of optical cavity detection regions. During operation, a system as disclosed herein is in contact with the fluid, and at least some components or objects of the fluid, including the analyte, can migrate onto or into the system. In the system are optical cavity detection regions, and the system also contains compounds that can modify one or more optical properties of an optical cavity detection region upon migrating in and out of the detection region, sometimes referred to as "optical property modifiers" or simply "modifiers". As used herein, an optical cavity detection region may be an area which is less than an entire optical cavity, or it may correspond to the optical cavity in its entirety.

The system also comprises a mechanism wherein the migration into and/or out of at least one detection region is regulated by an analyte, thereby providing a means for measuring changes in the analyte concentration. Regulation mechanisms with a degree of specificity for an analyte of interest are disclosed herein, resulting in systems for detecting concentration of an analyte in a fluid.

One type of desirable mechanism for regulating the migration of modifier in and out of an optical cavity detection region comprises a reservoir adjacent to the detection region. The reservoir is a region for storing modifiers that is separate from the optical cavity detection region. In embodiments, a receptor binds reversibly with a modifier in the said reservoir. More specifically, choosing a receptor-modifier pair with binding that is influenced by analyte, with some acceptable degree of specificity for the analyte, enables a useful embodiment of a mechanism. The receptors are constrained in some manner to remain within the reservoir to prevent their migration into the optical cavity detection region, the reservoir and detection region being separate. A system having such a mechanism responds to analyte as a result of changing ratio of "unbound" to bound modifier in the said reservoir, "unbound" in this case meaning not bound to receptor, the "unbound" modifier being available to migrate, e.g. by diffusion, into and back out of the optical cavity detection region. The migration changes the amount of modifier in the detection region and therefore changes at least one optical property of the detection region. In embodiments, there may be some leakage of receptor into optical cavity detection regions. As long as the leakage is slow enough that recalibration of a device and/or reference measurements can compensate for the leakage, such embodiments are still within the scope of the present application.

In the above mechanism, factors other than the unbound modifier can affect the optical properties of an optical cavity detection region. For example, temperature and components of the fluid other than the analyte that migrate into the optical cavity detection region may affect the optical properties. To mitigate the effects of these and other background factors, systems in this disclosure include at least a second optical cavity detection region into which the same components of the fluid may migrate. In operation, the optical properties of the said two or more detection regions are compared after detection, or alternatively a direct differential measurement of two or more detection regions is performed, in order to minimize the effect of background factors on the detection of analyte. Additional optical cavity detection regions may also be included in systems to account for background factors, including receptor leakage into detection regions, as disclosed in more detail below.

In some cases, there may exist compounds in the fluid other than the analyte that interfere with the mechanism for regulating the migration of modifier, i.e. "interfering compounds". For example, a fluid may contain objects or components other than the analyte of interest that compete with the binding of modifier to a receptor in the reservoir. In embodiments, systems may contain additional detection regions for detecting the presence of interfering compounds.

In embodiments, the system or a portion thereof is implanted into a living body, e.g. in or underneath the skin or in adipose tissue. In embodiments, the use of more than one detection region in a system, e.g. as described above, enables an implanted system to overcome previously encountered problems with optical detection of analytes. For example, failure mechanisms documented in the literature have included unacceptable sensitivity of a measurement to a variety of factors including temperature, pressure, variable tissue scattering, skin pigment variation, changes in hydration level, and interfering interstitial fluid (ISF) components.

In operation, optical cavity detection regions are illuminated, and light leaving the optical cavity is detected. For example, properties such as the intensity of the light versus wavelength or the spatial distribution of light intensity from an optical cavity detection region with optical property gradients may be detected. Based on the detected properties, the concentration, or changes in concentration, of analyte in the test fluid may be deduced.

In one embodiment light transmitted through at least one of the optical cavity detection regions also passes through a variable filter (i.e., an optical component), and the corresponding optical property being detected is the intensity of light transmitted through or reflected from the optical cavity detection region and the variable filter, as a function of location along the variable filter. The term "variable filter" refers to a filter of light with spatially variable filtering properties, e.g. spatially variable filtering wavelength.

The illumination source may be operatively associated with the optical cavities, e.g. by physical attachment to the container containing the optical cavity detection regions or by attachment to an optical fiber that is attached to the said container, or the illumination source may alternatively be located at a distance.

In one embodiment, a system detects the concentration of glucose analyte in a fluid by optically measuring the refractive index (RI) change in the detection region of a first optical cavity and comparing it to the refractive index change in a second optical cavity detection region. The second detection region is a reference region. Each optical cavity produces an optical transmission maximum at a wavelength that changes with multiple factors including temperature, salt and glucose concentration. By using a reference detection region along with the said first detection region, the detection can be made more specific to glucose. Determination of the refractive index from the wavelength of the cavity transmission maximum enables a precise determination of glucose, even at low levels.

In embodiments, the system confines a receptor within the reservoir. As mentioned, the binding of modifier to receptor should preferably be reversible such that a continuous monitoring of fluctuating levels of the analyte can be achieved. This reversibility is a particular advantage of the use of a binding mechanism in which the components of the assay are not consumed, in contrast to systems based on enzymatic and electrochemical detection of analyte in which analyte is consumed. Binding mechanisms are also preferred for reasons of safety as they do not generate unwanted products as might be generated by an enzymatic or electrochemical reaction. In some embodiments, the reservoir employs suitable barriers or membranes to contain receptors, such barriers or membranes arranged so that the modifier can readily diffuse between a detection region and the reservoir. In some embodiments, the receptor is kept within the reservoir by immobilization on a surface in the reservoir. In some embodiments, the receptor is kept within the reservoir by chemical or physical crosslinking, one example being crosslinking of receptor or receptor-containing components, and another example being covalent binding of receptor to a crosslinked gel within the reservoir.

Examples of suitable compounds for use as either receptors or modifiers in embodiments include, but are not limited to, antibodies or antibody fragments which retain an analyte or interfering compound binding site (e.g. Fab fragments), lectins (e.g. concanavalin A) that bind to an analyte or interfering compound, proteins with hormone binding sites, proteins with drug binding sites, catalytically inactive enzymes, aptamers, dextran, agarose, amylose, and molecularly-imprinted polymers.

An example of a system employing the concepts set forth above is a glucose sensor based on the competitive binding of glucose (analyte) and a receptor such as a dextran to a protein (modifier) with suitable specific binding sites. One such protein is the lectin, concanavalin A (Con A). Concanavalin A is a plant lectin originally extracted from the jack bean. It has one binding site for glucose per monomer of the protein. The glucose sensor is a bio-affinity sensor where the sensor's function depends on the relative affinity of the analyte (glucose) and receptor (dextran) for the modifier (Con A).

In this example, the system includes a container that includes a reservoir for the modifier and a separate optical cavity detection region. Analyte can enter into the container through one or more bounding regions. Preferably, the modifier should be a substance of higher molecular weight than the analyte such that it cannot freely diffuse out of a container, and in this example the Con A does indeed have a higher molecular weight than the glucose. In an alternative embodiment, the system might employ a glucose polymer such as dextran as the modifier and use Con A immobilized to the reservoir or to a gel within the reservoir as the receptor. The specificity of such glucose sensors in either class of embodiments is therefore based on Con A binding to glucose analyte.

The principle of operation of such glucose sensors is tied to the replacement of dextran in the dextran/Con A complex by glucose to form a glucose/Con A complex. In embodiments for which dextran is the receptor, the combined concentration of unbound Con A plus glucose/Con A complex increases with an increase in glucose concentration. Since the unbound Con A and glucose/Con A complex can migrate to the optical cavity detection region, the concentration of Con A modifier in the optical cavity detection region will increase, thereby changing an observable optical property.

In an alternative design example, Con A is immobilized in the reservoir and therefore outside the view of the detector, and dextran is added as the optical property modifier. Thus the detector will respond primarily to the concentration of dextran not bound to Con A, which increases with increasing glucose concentration.

The described sensor can be adapted for the detection or quantitative measurement of other analytes present in bodily fluid. Preferred analytes include glucose (in connection with the long-term monitoring of diabetics), urea (in connection with kidney disease or dysfunction), lactate (in connection with assessment of muscle performance in sports medicine), ions such as sodium, calcium or potassium and therapeutic drugs whose concentration in the blood must be closely monitored, such as, for example, insulin, digoxin, theophylline or immunosuppressant drugs. The above analytes are listed by way of example only and it is to be understood that the precise nature of the analyte to be measured is not to be limited by the description herein.

II. Environment

FIG. 1 schematically illustrates general features of product 10, an example of an implantable article or system with which the concepts of the present application are implemented in various embodiments as described in greater detail below. Product 10 involves a combination of parts or components. For example, product 10 includes first part 12 and second part 14. In the illustrated implementation, parts 12 and 14 are connected along dashed line 16, which can be the result of being fabricated or joined together.

Parts 12 and 14 include containers 20 and 22, respectively, illustratively connected in a structure that includes wall-like parts 24, 26, and 28, with wall-like part 24 connecting parts 26 and 28 and being between containers 20 and 22. The respective boundary of each of containers 20 and 22 illustratively includes one or more bounding regions through which objects in bodily fluid can transfer between interior and exterior of the container, i.e., can enter and/or exit. Such bounding regions are sometimes referred to herein as "object transfer regions", in contrast with bounding regions that are closed; a closed or sealed container would have no object transfer regions. Although object transfer regions could have any shape and could include any appropriate structures through which objects can transfer, the net effect of all such object transfer regions is summarized for container 20 by opening 30 and for container 22 by opening 32; in exemplary implementations described below, containers may have any suitable number of object transfer regions, which may include various fluidic components that permit diffusion and flow of objects and perform filtering, pumping, and so forth.

Each of parts 12 and 14 is also operable as a respective optical cavity. The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" is a component that includes one or more optical cavities.

In the exemplary implementation of FIG. 1, each part's optical cavity operation can arise in a respective light-transmissive region between light-reflective regions of wall-like parts 26 and 28. The respective light-transmissive region of part 12 can include at least part of container 20, and that of part 14 can similarly include at least part of container 22. Therefore product 10 includes an "optical cavity structure", meaning a structure with parts or components that can operate as an optical cavity.

In operation as optical cavities, each of parts 12 and 14 can illustratively receive input light through a surface of wall-like part 26 as indicated by arrows 40 and can provide transmitted output light through a surface of wall-like part 28 as indicated by arrows 42 and reflected output light through a surface of wall-like part 26 as indicated by arrows 44. The surfaces through which input light is received (sometimes referred to as "entry surfaces") and through which output light is transmitted or reflected (sometimes referred to as "exit surfaces") can, however, be somewhat arbitrary, and it may be possible in some implementations to reverse direction of input and output light or to have multiple entry or exit surfaces; the term "light interface surface" is therefore used herein as a generic term that includes any of these types of entry and exit surfaces.

As shown in FIG. 1, light interface surfaces of the first and second parts 12 and 14 can be aligned so that they can receive input light from the same light source (not shown) and can similarly provide output light to the same photosensing component (not shown), whether photosensing output light from transmission modes or reflection modes. In general, light interactive surfaces are "aligned" in a given application with one or both of an external light source and an external photosensing component if they are in approximately the same plane or other surface such that input light from the application's external light source is received similarly on both surfaces and/or output light to the application's photosensing component is provided similarly from both surfaces.

Broadly, optical components for guiding light into the optical cavities include light interface surfaces, parts having light interface surfaces, parts or components that aid in aligning illumination sources and/or photosensing components, lenses, gratings, slits, fiber optic fibers, and any other components that enable or improve the guiding of a desired illuminating light wave into an optical cavity (e.g., ultraviolet (UV) illumination, infrared (IR) illumination, visible wavelength illumination). In embodiments, a system for detecting concentration of an analyte may contain one or more such components. UV absorption is known to be a reliable way to measure protein concentration, particularly at wavelengths in the range of 220 to 320 nanometers. Near IR illumination is useful in the wavelength range of 750 to 1500 nanometers. In part as skin is known to be reasonably transparent at wavelengths in that range. A second reason for use of this near IR wavelength range is that VCSELs are available at wavelengths that lie in this range.

Within the broad category of optical cavities, there are various more specific types: For example, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light, or providing attenuated output light, with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered as "reflection modes". Similarly, a transmissive cavity can be described as "illuminated at" a mode by any operation that provides input light that results in transmission of output light in the mode's photon energy subrange.

In typical implementations of optical cavities, two light-reflective components have approximately parallel reflection surfaces and the light-transmissive region is sufficiently uniform that measurements would indicate more than one reflection of light within the light-transmissive region. Such cavities define a directional orientation as follows: Directions in which light could propagate and be reflected more than once within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not necessarily perpendicular to entry surfaces or reflection surfaces. Light incident on a transmissive cavity's entry surface, not necessarily perpendicular to this surface, is reflected more than one time within the cavity, producing transmission modes in accordance with the cavity's geometry. But transmission modes are affected by angle of incidence: Depending on the type of cavity and the angle of incidence, modes can be red shifted (i.e., an increase in wavelength) in comparison to perpendicular incidence; if all light enters a cavity at approximately the same angle, performance is affected only by the shifting of modes and modes are not also broadened, but performance is reduced if a cavity receives incident light distributed across an angular range because transmission mode structure is then averaged over multiple angles. It is also noted that aperture size, surface roughness and tilt angles between the mirrors change the full-width-half-maximum ("FWHM") and absolute intensity of transmission modes.

The term "object" is used herein in the general sense of anything that can affect an optical characteristic, whether a characteristic of emission (e.g. radiation, fluorescence, incandescence, luminescence, etc.), scattering (e.g. reflection, deflection, diffraction, refraction, etc.), or other types of light transmission. The optical characteristic is "affected by presence of" or is simply "affected by" the object.

Examples of objects that could occur in implementations as described below include single molecules, agglomerated molecules, molecule clusters, cells, viruses, bacteria, proteins, DNA, microparticles, nanoparticles, and emulsions. Objects, also at times called components, may absorb light in the cavity, so that its content reduces the reflection or scattering of the light; in this case, an object could be an "absorbent component" of a fluid. Or a fluid may include objects that scatter incident light in a way that depends on photon energy, so that the light in the optical cavity is scattered correspondingly; in this case, an object could be a "scattering component". An analyte (i.e., a chemical species being investigated) in an optical cavity can act as a fluorescent, absorbent, scattering, or in particular RI-changing, component.

Some implementations as described below involve groups of objects that are treated as interchangeable because of some shared characteristic, with such a group of objects being referred to herein as a "type" of objects. For example, all molecules that satisfy a criterion for being glucose molecules can be treated as the same type of objects, i.e., the type "glucose". More generally, all objects that are examples of a chemical species being investigated are examples of an "analyte type".

A type of object is "present in", "positioned in", or simply "in" an optical cavity when a sufficient quantity of objects of the type are in all or some part of the cavity's light-transmissive region to have a measurable effect on an optical characteristic of the optical cavity. An optical cavity provides "object-affected output light" if the optical cavity's output light is different in some way when a type of objects is present in the cavity than when the type of objects is absent, with the difference being due to the effect of the type of objects on the cavity's optical characteristics.

An object "is transferred" or "transfers" between a container's exterior and interior if the object moves between the container's exterior and interior by entering and/or exiting at least once. For example, the object could be conveyed between exterior and interior by flow of a bodily fluid in response to pressure from a pump or other pressure source, in which cases the object may be referred to as being "carried" by the bodily fluid; or the object could be conveyed between exterior and interior as a result of diffusion due to a concentration or free energy gradient of objects of its type in a bodily fluid, in which case the object may be referred to as "diffusing" in the bodily fluid.

Various techniques can be used to control rates of transfer of objects that are carried or diffusing in bodily fluid. In general, control techniques can cause different types of objects to be transferred at different rates.

As a result of the addition of an optical property modifier into one cavity that provides specificity to a target analyte, parts 12 and 14 in FIG. 1 have different optical characteristics when operating as optical cavities. As an illustration of the different optical characteristics, Box 50 at the ends of arrows 42 contains a graph, illustrating that the optical cavities of the first and second parts 12 and 14 each have a set of transmission modes in which they transmit output light, with intensity functions of two transmission modes of container 22 being illustrated by solid-line curve 52 and those of counterpart modes of container 20 being illustrated by dashed-line curve 54. The difference between curve 52 and curve 54 provides a measure of the concentration of analyte because the analyte affects the migration of modifier into the corresponding optical cavity detection region. Similarly, box 60 at the ends of arrows 44 contains a graph, illustrating that the optical cavities of the first and second parts 12 and 14 each have a set of reflection modes in which they reflect output light, with intensity functions of two reflection modes of container 22 being illustrated by solid-line curve 62 and those of counterpart modes of container 20 being illustrated by dashed-line curve 64. Similarly to curves 52 and 54, the difference between curves 62 and 64 changes in response to changes in analyte concentration through the effect of analyte on the concentration of optical property modifier in the corresponding optical cavity detection region.

The term "intensity function" refers to a function that relates intensity of output light to another parameter, such as photon energy for an "intensity-energy function" or, in some implementations, position along a light interface surface or a photosensitive surface. An intensity function can have any of a wide variety of shapes and features, but a shape that frequently arises in transmission modes is the "peak", a shape characterized by a local maximum value from which a curve for the function slopes downward. Peaks have various features, including "central value", meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). Reflection modes have similar features, though typically with valley-like dips, sometimes referred to as "valleys", and plateau-like reflection bands between the valleys, approximately complementary to the counterpart transmission modes; therefore, each valley in the reflection intensity function has a central energy and an FWHM similar to those of the counterpart peak in the transmission intensity function.

Features such as transmission mode peaks and reflection mode valleys are examples of optical characteristics, also at times referred to herein as optical properties. More specifically, "optical spectrum characteristics (or properties)", "optical spectrum features", or simply "spectrum characteristics (or properties)" are examples of optical characteristics that appear in functions such as intensity-energy functions that depend on photon energy, represented in boxes 50 and 60 by the horizontal axes indicating, e.g., wavelength or frequency; positions on such axes may be referred to as "spectral positions". As shown in FIG. 1, the central energies of the peaks and valleys may be displaced along the respective horizontal axes between spectral positions, e.g., peaks in curves 52 and 54 in box 50 are displaced from one another and valleys in curves 62 and 64 in box 60 are displaced from one another. These displacements or "shifts" are caused by differences in contents of containers 20 and 22, resulting from migration of modifier in one container from a reservoir (not shown in FIG. 1) into an optical cavity detection region. The other container is devoid of modifier in this embodiment. More specifically, the shifts result from certain objects that affect the spectrum characteristics, including analyte, modifier, and various others. An object that affects a spectrum characteristic of an optical cavity is sometimes referred to herein as a "spectrum-affecting object". Output light from an optical cavity that is affected by a spectrum-affecting object is sometimes referred to herein as "spectrum-affected". Similarly, the term "shift" refers herein to any displacement of a spectrum characteristic or feature with respect to photon energy, e.g. wavelength, frequency, or phase; a "spectrum-shifting object" shifts a spectrum characteristic or feature, e.g. with respect to wavelength, frequency, or phase; and cavity output light in which a spectrum characteristic or feature is shifted is "spectrum-shifted".

In general, information can be encoded in one of these features. The encoding can be accomplished not only in shifts, but also in various other ways, including, for example, absorption effects such as reduced maximum intensity or contrast or an altered FWHM. Encoding techniques involving such effects are described in co-pending U.S. patent application Ser. No. 111,702,363, entitled "Encoding Optical Cavity Output Light" and incorporated herein by reference in its entirety. Once encoded, such information can also be recovered in various ways, including those described in co-pending U.S. patent application Ser. No. 11/702,249, entitled "Obtaining Information From Optical Cavity Output Light" and incorporated herein by reference in its entirety.

As a result of these features, product 10 can be used in applications in which optical characteristics affected by contents of container 20 are compared with those affected by contents of container 22. Furthermore, product 10 can be implanted within the body, allowing analytes to enter and exit from containers 20 and 22, such as analytes from blood, lymph, or interstitial fluid (ISF), and continuous monitoring is possible using this technique.

The curves in boxes 50 and 60 in FIG. 1 are typical of intensity-energy curves that could be obtained from operation of a "homogeneous optical cavity", meaning a cavity whose light-transmissive region includes an extended part with substantially constant optical distance between its reflection surfaces. Each curve is an intensity-energy graph or "output spectrum" for the respective optical cavity's operation.

Each of the transmission mode peaks could be referred to as an "intensity-energy peak" or simply "intensity peak" that results from a respective transmission or reflection mode. The maxima of intensity-energy peaks (and minima of the counterpart reflection mode valleys) are spaced apart as a function of photon energy (e.g. wavelength), and the difference between the central energy of adjacent transmission mode peaks is referred to as "free spectral range" or "FSR".

The wavelength $\lambda$ of each intensity-energy peak can be obtained from $\lambda(k)=2nd/k$, where n is the refractive index of the cavity, d is cavity thickness, and k is a non-zero integer in the case of light entering the cavity perpendicular to the reflective elements. Therefore, if refractive index of the cavity changes, $\lambda(k)$ also changes for a given value of k, so that if a peak's central energy changes by $\lambda+$ and $\lambda-$, the change provides information about refractive index change. Similarly, the intensity of the peaks depends on absorption in the cavity, so that if the intensity of a peak departs from its maximum, the change provides information about absorption change.

Many of the exemplary implementations described herein operate as homogeneous optical cavities, but similar techniques can be applied to products comprising one or more "inhomogeneous optical cavity", meaning a cavity that does not meet the above definition of a homogeneous optical cavity. In general, further information about homogeneous and inhomogeneous optical cavities and about techniques for encoding information in their optical characteristics is provided in co-pending U.S. patent application Ser. No. 11/702,363, entitled "Encoding Optical Cavity Output Light" and incorporated herein by reference in its entirety.

Various techniques can be used to produce laterally varying energy distributions with inhomogeneous optical cavities having laterally varying optical thicknesses and, even with homogeneous optical cavities, with angled illumination from a point light source rather than perpendicular illumination; several techniques are described in U.S. Pat. No. 7,291,824, incorporated herein by reference in its entirety.

One implementation of a Fabry-Perot optical cavity is as a Fabry-Perot interferometer or etalon, which is typically made of a transparent plate with two partially reflecting surfaces, or two parallel, partially reflecting mirrors. Technically, the former is an etalon and the latter is an interferometer, but the terminology is often used interchangeably. Its transmission spectrum as a function of wavelength exhibits peaks of large transmission corresponding to resonances of the etalon.

In one embodiment of the system of FIG. 1 a double container Fabry Perot etalon is used to measure the RI difference (or shift) between the two containers. The concept of RI detection with Fabry Perot etalons has been described in previous applications including U.S. Ser. No. 11/957,610, "Controlling Transfer Of Objects Affecting Optical Characteristics". Briefly, this application discusses the use of two containers of an identical Fabry-Perot etalon, which are sampled with monochromatic laser light. The spectral positions of the light transmission maxima through the containers depend on the RI of the materials inside the containers. The wavelength is swept by a single-mode vertical-cavity surface-emitting laser (VCSEL) by current tuning in order to determine the position of the transmission maxima. The VCSEL beam is collimated and split up into two parallel beams, each one of them directed into one container of the etalon. The current sweeping of the VCSEL results in a linear wavelength sweeping. The transmission of the etalon containers is detected by two photo detectors. The temporal distance of two transmission maxima (of the same order) is linearly dependent on the RI difference (or shift) between the two containers. By this method refractive index differences between the containers can be detected with an accuracy of approximately $\Delta n=3*10^{-6}$. In an aqueous glucose solution this translates into a glucose concentration change of 2 mg/dl (physiological range of non-diabetic individual: 70 mg/dl to 200 mg/dl, physiological range of diabetic individuals: 40 mg/dl to 400 mg/dl). As can be inferred from Table 1, RI measurements in the ISF are influenced by the variations of different components. Glucose concentration changes however have the largest influence on RI changes and therefore is an object amenable to detection.

TABLE 1

ISF Components Affecting RI

| Analyte | ISF concentration change | $\Delta n_{medium}$ $(10^{-6})$ | Variation Rate | Weight g/mol |
|---|---|---|---|---|
| Glucose | ±5.6 mmol/L | 140.9 | Fast | 180.16 |
| Creatine | ±0.3 mmol/L | 6.633 | Slow | 131.13 |
| Lactic acid | ±1.3 mmol/L | 9.906 | Slow | 90.08 |
| Serum Albumin | ±1.5 µmol/L | 18.47 | Slow | 67000 |
| NaCl | ±1 mmol/L | 10.1 | Slow, except for dehydration | 58.44 |

III. Detailed Discussion of Device and Method

Having discussed the general concepts of a device capable of detecting and measuring objects located within a fluid, such as ISF, described below is a method and device that enables the selective amplification of the contribution of specific types of small (<10 kDa) molecules for measurement including but not limited to index of refraction (RI) measurements. The following description focuses on, but is not limited to providing glucose specificity in RI measurements in an implantable continuous glucose monitor (CGM).

In one embodiment, this application describes a CGM where glucose (an analyte, also an object) from the interstitial fluid (ISF) diffuses into the CGM and specifically binds to a target molecule, such as Concanavalin A. Concanavalin A (Con A, 26.5 kDa monomer) binds to dextran (the receptor) held within a reservoir (which will be described in more detail below). Competitive binding of glucose to Con A decreases the amount of Con A bound to dextran. The free Con A (i.e. not bound to glucose or dextran) and the Con A-glucose complex then diffuse into the measurement region of the CGM, increasing the RI in the optical cavity detection region (which will be described in more detail below) by the additive effects of the increased concentration of Con A-glucose complex and free Con A. Thus, Con A acts as an optical property modifier, also more simply called a modifier herein. By this design the RI change of a single glucose molecule (180 Da) is amplified by a factor of about 150 times, the ratio of the molecular weight of a Con A monomer to the molecular weight of glucose. When comparing the RI of this optical cavity detection region to the RI of another optical cavity detection region which excludes large molecules (i.e. Con A), the RI difference between the two regions is (selectively) proportional to the glucose concentration in the test fluid (i.e. ISF). This RI difference is much less sensitive to factors such as temperature, pressure, and compounds in ISF that affect RI (see Table 1) than the RI of either region alone, since those factors have approximately the same effect on the RI in both regions. This is an advantage of a differential measurement.

It is to be appreciated the described process is reversible. Particularly, as the free glucose concentration in the CGM drops, the Con A-glucose complex concentration drops and the amount of Con A bound to dextran in the reservoir increases. Thus, a device of the present application is constructed such that repeated binding and re-binding of Con A modifier in the reservoir is achieved, which allows continuous monitoring of an analyte in a fluid.

Con A is used in this embodiment as it is known to chemically selectively bind to sugars (e.g. glucose, mannose and dextran, a polysaccharide comprised of glucose molecules). It does not bind, or binds with a lower affinity, to other objects in the ISF. Therefore, in this example, Con A binds at a first or higher affinity to certain sugars, but does not bind or binds at a lower or second affinity to other objects in the fluid. As will be discussed below, other receptors may be used to provide even different affinities of binding between the different sugars. For the competitive binding between glucose and dextran to Con A, special forms of crosslinked dextran, in the form of beads, is commonly utilized. Examples include products with the tradename Sephadex. Sephadex beads are available in different bead diameters up to 120 μm.

Figure 2:
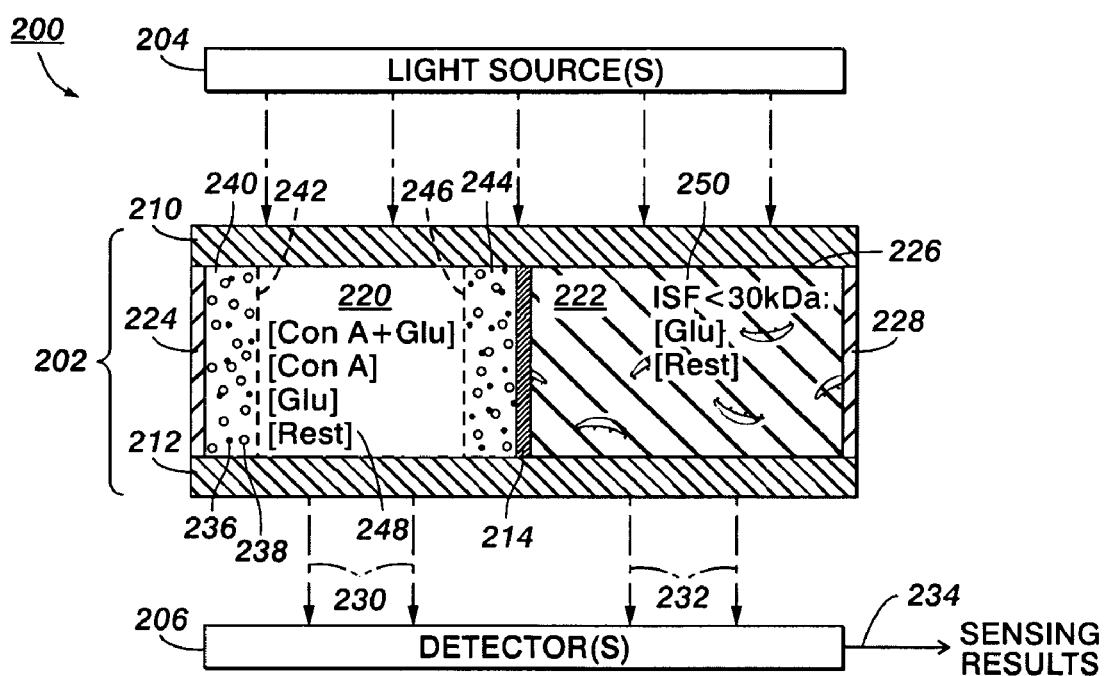
FIG. 2 is a schematic diagram of an implementation of a system that can include an article as in FIG. 1.

Turning now to FIG. 2, illustrated is a system which incorporates the concepts of the present application as has been described above, including concepts to refine the transmission of the objects to be measured.

System 200 illustratively includes optical cavity analyte detection component 202, light source component 204, and detector component 206, with the implantable product including at least optical cavity component 202, possibly in combination with one or more other optical cavity analyte detection components. The detector component 206 may be one or a plurality of components (at times called detecting means) and may include but is not limited to photodetectors. Additionally, in one embodiment the illumination (light) source and detecting means may be placed in optical contact by use of optical fibers. Still further, in another embodiment the detecting means may be comprised of an RF signal from the system, which is received by an RF receiver.

Optical cavity analyte detection component 202 could be an implementation of implantable product 10 in FIG. 1 in a long, narrow structure as described below in relation to exemplary implementations. A compact device with such a structure could be inserted in a minimally invasive manner in or under a human's skin to enable continuous detection of glucose without further invasive procedures.

In the illustrated example, optical cavity component 202 is shown in cross-sectional view, illustrating how light-reflective components 210 and 212 and a set of wall parts including wall 214 define containers 220 and 222 between light-reflective components 210 and 212. Each of containers 220 and 222 and bounding surfaces of components 210 and 212 can operate as a respective Fabry-Perot (FP) interferometer or etalon (also called an FP optical cavity), for example, with the objective of obtaining values indicating concentration of glucose in surrounding fluid. For example, in some exemplary implementations described below, indices of refraction of small samples from surrounding interstitial fluid are measured, with each sample being contained within a FP optical cavity and the resulting output signal only being influenced substantially by changes within the sample.

The cross section of FIG. 2 could be taken at a point along the length of the structure at which, when implanted under a human's skin, objects in interstitial fluid can transfer between the exterior and interior of each of first (or specificity) container 220 and second container 222 through respective filters described in more detail below. In each case, each container's respective filters are shown in its side wall disposed away from the other container, and could, for example, be mounted or otherwise attached to or connected in any suitable combination of one or more openings of any appropriate shape and size along the length of a container's side wall and/or in one or both of a container's end walls; these examples are merely illustrative, and filters could be mounted or otherwise attached to or connected in or through any appropriate part of the boundary (or boundary regions) of the container and in any appropriate way.

Container 220 is bounded by reflective surfaces of components 210 and 212 and also by a surface of wall 214; it can contain interstitial fluid filtered by filter 224. Container 222 is similarly bounded by reflective surfaces of components 210 and 212 and also by the opposite surface of wall 214; it can contain interstitial fluid filtered by filter 228. Container 222 is shown with interstitial fluid filling its interior, except that any species larger than 30 kDa have been filtered out by filter 228. However, for clarity of description, interstitial fluid is not illustrated in container 220. Rather, such fluid and other objects in detection/measuring area or region 248 are designated by identifiers [Con A+Glu], [Con A], [Glu] or [Rest], where [Rest] represents items of the interstitial fluid, filtered through filter 224, other than glucose [Glu], [Con A] representing free Con A, and [Con A+Glu] representing a Con A-Glucose complex.

Each of filters 224 and 228 prevents a subset of objects in the ISF that can affect optical characteristics from being transferred into containers 220 and 222 at a relatively rapid rate. In some successful implementations, filters 224 and 228 have been implemented as macromolecule or molecular weight cut-off (MWCO) filters that effectively prevent molecules over an appropriate size such as about 15-30 kDa from entering containers 220 and 222, respectively. Filters 224 and 228 could be implemented in various other ways. As a result of filters 224 and 228, transfer of objects such as large molecules, cells, and so forth occurs only at a relatively slow, negligible rate or possibly does not occur at all if filters 224 and 228 are highly effective. In one embodiment the filters may be a dialysis membrane.

To achieve glucose specificity in RI measurements, all openings of the containers (cavity) are covered with an identical membrane, for example a membrane within the range of 10-100000 Da MWCO, more specifically a membrane with a 3-30 kDa MWCO, and even more specifically for exemplary purposes a membrane with a 15 kDa MWCO (i.e., filters 224 228). This prevents large molecules (e.g. Serum Albumin, Table 1) from entering the interior of the containers, while allowing small molecules (NaCl, Glucose etc.) to diffuse into them. Con A 236 (Free Con A, Con A bound to dextran in the form of Sephadex beads 238, or Con A bound to glucose) is/are located and kept inside the specificity container 220 by use of the same membrane. Dextran beads are confined within the reservoir 240 by filter (or container filter) 224 and a mesh (or reservoir filter) 242, and in another reservoir area 244 defined by wall 214 and mesh (or reservoir filter) 246. Still further, in some embodiments the size of the filter may be approximately 1-6 nanometers, large enough to allow small molecules to pass while blocking large proteins, cells, and other large objects.

From the ISF, molecules less than 15 kDa diffuse into both optical cavity detection regions 248, 250 of the containers 220, 222. The reservoir areas 240, 244 of the specificity container 220 are partly filled with Sephadex beads 238 which are inhibited from leaving the specificity container due to the use of the filters (e.g., container filter in the form of MWCO membranes). At the same time the beads also cannot enter the optical cavity detection region 248 of the specificity container 220, because mesh (bead diameter >pore diameter) 242, 246 seals the optical cavity detection region 248 from the reservoir regions 240, 244. Thus, the optical cavity detection region 248 and the reservoir regions 240,244 define separate areas of the specificity container 220. Previous to being placed into the reservoir area, the beads have been swollen in a suitable buffer (e.g. TRIS, PBS etc. at pH 7.4, buffer contains Ca and Mg salt) which also contained Con A. By this operation the Con A is bound to the beads. Thus the beads store the Con A. As mentioned above, Con A is released from the beads when glucose diffuses into the storage region of the specificity container, as glucose competitively (with respect to dextran) binds to Con A. The resulting Con A-glucose complex, as well as any free Con A, can then diffuse through the mesh (where the pore diameter is greater than the Con A diameter) 242, 246 into the optical cavity detection region 248 of the specificity container.

The concentration of the released Con A-glucose complex is dependent on the free glucose concentration in the specificity container. This concentration also equilibrates with the free glucose concentration in the ISF so that the free glucose concentration within the container is not affected by the "glucose uptake" of Con A.

The RI difference between the two measurement regions in the two containers is comprised of the concentration difference of Con A (free and bound to glucose) in the specificity container versus no Con A in the reference container; this concentration difference is a measure for free glucose in the ISF. A straightforward procedure for correlating the RI difference to actual glucose values is to use a fluid with a known glucose value, and then the corresponding RI difference is identified as representing that glucose value. This process is repeated to obtain as many data points as necessary.

In one embodiment the use of the filter (MWCO) and mesh is not only to exclude objects that are larger than, for example, 15 kDa (depending on filter size) from the specificity container. Rather, they are also used to maintain the receptors and modifiers within the specificity container. For example, in the described glucose sensing application, it is the Con A, as well as the Sephadex beads, which are maintained in the specificity container by use of the filters 224.

As the Con A is much bigger than the glucose, combining them results in an amplification of the RI signal due to glucose alone of approximately 150 (i.e., approximately the ratio between the molecular weights of Con A and glucose).

To obtain a useful signal of this amplified RI change, the system is tuned by taking into account the amount of Con A put into the system, the binding affinity between the Con A and glucose, and the binding affinity between the Con A and the beads.

The amount of glucose which binds to Con A is correlated to the amount of glucose present in the ISF. Therefore the amount of release of Con A will be correlated to the amount of glucose in the system.

In operation, optical cavity detection region 248 and the optical cavity detection region within container 222, receives input light from light source component 204. Examples of light sources include one or more tunable lasers such as VCSELs, DFB lasers, DBR lasers, solid state lasers more generally, resonant cavity LED's, or other appropriate light sources as described above. In response, optical cavity component 202 operates with two parallel optical cavity detection regions, each of which provides output light to detector component 206, which has been successfully implemented with a separate photosensing detector for each cavity: One optical cavity detection region within container 220 provides output light, represented by arrow 230, with information about the contents of container 220; the other optical cavity detection region within container 222 provides output light, represented by arrow 232, with information about the contents of container 222. For example, if the optical cavities both operate as Fabry-Perot interferometers or etalons or as similar optical cavities with transmission or reflection modes, features of the modes of the two cavities will differ in a way that indicates difference of refractive index of contents of the respective containers. At the same time, the modes of the two cavities will be affected identically by some variations, such as variations in electrolyte concentration or in temperature, so that the spectral position difference between their modes will not be affected by such variations. As a result, second container 222 serves as a reference in the differential measurement, with variation in Con A-glucose complex concentration, and free Con A being the predominant cause of differences between spectral positions of the modes of the two cavities. In alternative embodiments, the intensity of light transmitted through the optical cavities is measured and the difference in absorption coefficients for the matter in the detection regions deduced. In yet other embodiments with birefringent modifiers, the polarization of light transmitted through the optical cavities is measured and the difference in birefringence properties of the two optical cavity detection regions is deduced.

In response to output light from the optical cavities, the photosensing detectors in detector component 206 obtain sensing results that can include information about, for example, indices of refraction or absorption coefficients of contents of both containers, and the sensing results can be provided to an external component such as a CPU or other processor, as indicated by arrow 234. The central processing unit (CPU) or other processor can use the sensing results to obtain information about glucose concentration, such as in one of the ways described below. It is important to note that correlation of the sensing results to glucose concentration does not necessarily require the actual deconvolution of a material property such as index of refraction or absorptivity from the sensing results. Rather, the important concept is that the optical property being measured, e.g. intensity or polarization of transmitted light, depends on the nature of the material in the optical cavity detection region and can therefore be correlated to changes in the material properties.

In a typical implementation, objects could be transferred into containers in component 202 by diffusion or, if pumping or the like were implemented, by being carried by flow of bodily fluid, but if power is available in the implantable product for other operations as described below, electrochemical or electromechanical transport processes could also be implemented to manipulate flow of bodily fluid, such as to assure representative sampling or to extend the operational life of the implantable product, and such processes could also be controlled by a processor. Power could be available in many possible ways, including, for example, by inductive coupling, from one or more batteries, or from one or more photocells or other electromagnetic receivers.

Figure 3:
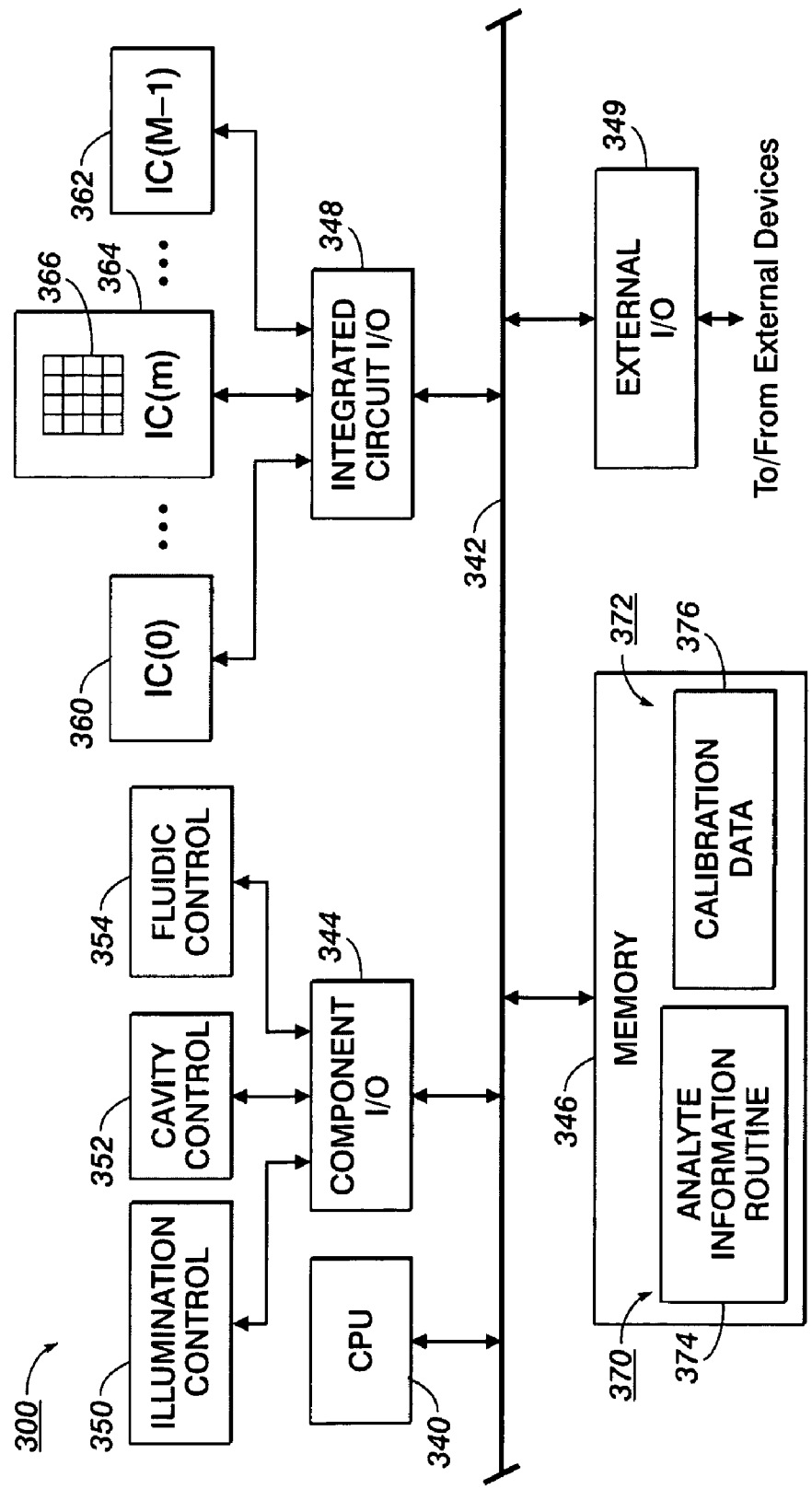
FIG. 3 is a schematic circuit diagram of an implementation of a system with components like that in FIG. 2.

FIG. 3 illustrates electrical components that can be used in implementing a system such as system 200 of FIG. 2. System 300 of FIG. 3 illustratively includes central processing unit (CPU) 340 connected to various components through bus 342, but a wide variety of other architectures could be employed, including any appropriate combination of hardware and software, as well as specialized hardware components such as application specific integrated circuits (ASICs) for one or more of the illustrated components or in place of a software component executed by CPU 340.

System 300 also includes component input/output (I/O) 344, memory 346, integrated circuit input/output (IC I/O) 348, and external I/O 349, all connected to bus 342. System 300 can include various other components (not shown) connected to bus 342. In addition to connections through external I/O 349 by which signals can be provided to and received from external devices, bus 342 can also be connected directly to components outside of system 300.

Component I/O 344 permits CPU 340 to communicate with certain components of system 300, illustratively including illumination control 350, cavity control 352, and fluidic control 354 and further external sensors such as temperature sensors and conductivity sensors. For interactive applications, component I/O 344 could also be connected to a suitable user interface, such as a monitor and keyboard (not shown) or regulatory components such as an insulin pump. In the exemplary implementation in FIG. 2, illumination control 350 can include light sources 204 (FIG. 2) and circuitry for controlling them; cavity control 352 can include electrodes or other components that can be operated to control cavity 304 and other cavities and can also include circuitry connected to those components; and fluidic control 354 can similarly include pumps or other fluidic devices or components that can operate to modify fluidic transfer into, through, or out of one or both of containers 220 and 222 (FIG. 2), and can also include circuitry connected to those devices and components.

In the illustrated implementation of system 300, integrated circuit input/output (IC I/O) 348 is a similar I/O component that permits CPU 340 to communicate with one or more ICs, such as in detector 206 in FIG. 2. A number of ICs are illustrated by a series from IC(O) 360 to IC(M-1) 362, including IC(m) 364 with at least one photosensor such as a single discrete photosensor or with exemplary array 366.

Memory 346 illustratively includes program memory 370 and data memory 372, although instructions for execution by CPU 340 and data access during execution of instructions could be provided in any suitable way, including through external devices or components. The routines stored in program memory 370 illustratively include analyte information routine 374. In addition, program memory 370 could store various additional routines and also subroutines (not shown) that CPU 340 could call in executing routine 374. Similarly, the data in data memory 372 illustratively include calibration data 376, but could include various additional items of data and data structures accessed by CPU 340.

In executing routine 374, CPU 340 can provide signals to cavity control 352 and to analyte control 354 so that an analyte is present in cavity 202 (FIG. 2), for example, with the analyte having optical characteristics that affect output light from device 202. It is to be appreciated in embodiments where analyte control is used, a pump or other motivating mechanism is provided to move analyte. However, if a pump, etc. is not part of the system, analyte control would not be needed. CPU 340 can also provide signals to illumination control 350 so that cavity 202 is appropriately illuminated to provide spectrum-affected output light. CPU 340 can also provide signals to each of ICs 360 through 362 to obtain sensing results that include information about the analyte in cavity 202. In an implementation with a position-sensitive detector (PSD), CPU 340 could instead provide whatever signals are necessary to obtain photosensed quantities from the PSD; for example, CPU 340 could control circuitry to connect output currents from the PSD to a differential amplifier.

Figure 4:
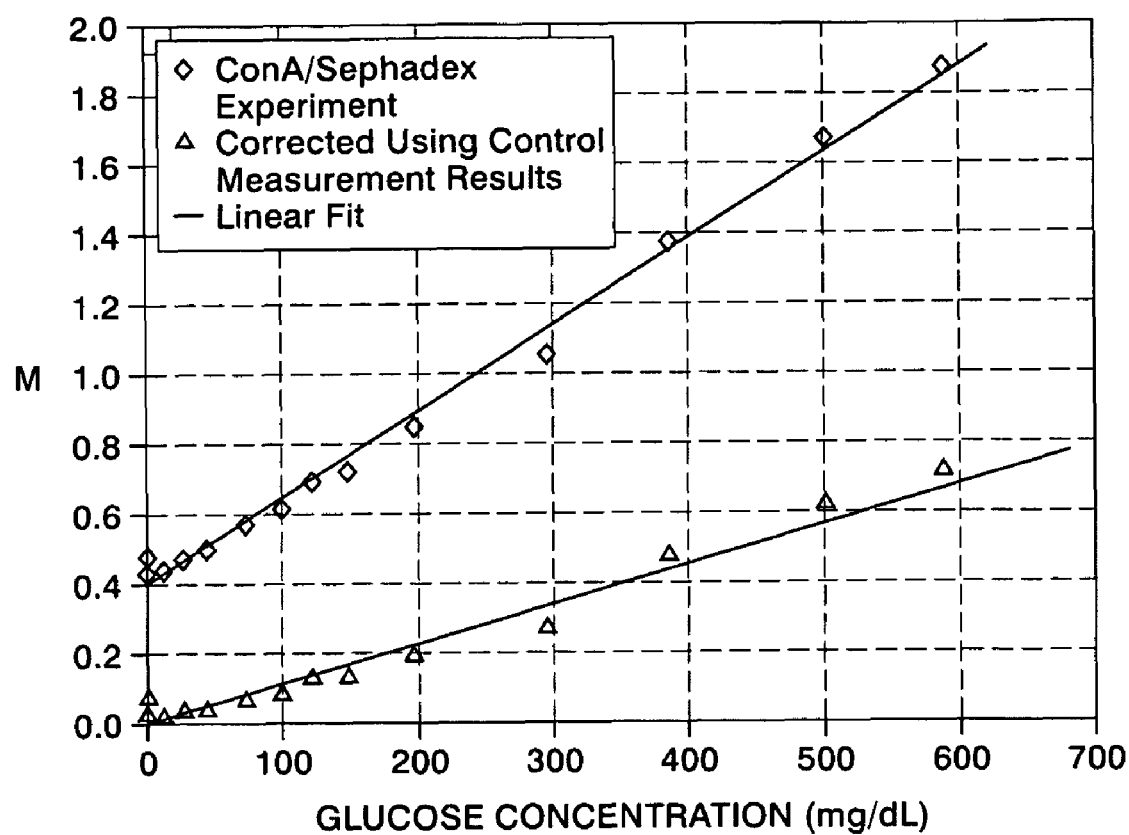
FIG. 4 is a graph showing data on sensitivity/specificity.

Turning to FIG. 4, illustrated is data showing that Con A binding to Sephadex receptor can be affected by glucose and that the Con A released from the Sephadex gives an optical signal that indicates the concentration of glucose. In each measurement, Con A bound to Sephadex beads was equilibrated in phosphate buffered saline (PBS) with calcium chloride and magnesium chloride (Dulbecco's PBS). Next, a given amount of glucose was added, and the mixture allowed to reach a new equilibrium. Then the Sephadex beads, including any bound Con A, were physically separated, leaving a sample free of the beads. The sample was introduced into one etalon optical cavity detection region (the "sample" region), and buffer was introduced into a second etalon optical cavity detection region (the "reference" region). The intensity of light transmitted through the detection regions as a function of wavelength was measured, modeling the measurement that would be done in embodiments of the disclosed invention in an optical cavity detection region. The two optical spectrum curves were compared. Specifically, the spectral position of the peak of a first mode for both the sample and buffer was determined, and the difference in these two spectral positions, also called the "shift", was calculated. The difference in spectral positions of the peaks of the said first mode and an adjacent second mode, the free spectral range or FSR, was also determined, and the shift was divided by the latter difference to yield the quantity "M" in FIG. 4. A value of M=1 corresponds to a shift equaling the free spectral range. FIG. 4 shows results for M versus glucose concentration. In control experiments, glucose solutions were prepared in the absence of Con A and Sephadex, and measurements of these solutions were performed using the same sample optical cavity and reference optical cavity as before. The results as a function of glucose concentration were subtracted from the Con A/Sephadex results to yield the "corrected" results in FIG. 4. The non-zero correction at zero glucose concentration occurs because the sample optical cavity is not perfectly identical to the reference optical cavity, resulting in different measurements of M for buffer in the two different cavities. As can be seen, the Con A concentration correlates to the glucose concentration. Particularly, the diamonds illustrate the signal that was found when the quantity M was measured, and the triangles show the effect when the RI of glucose in the absence of Con A/Sephadex is subtracted. These data illustrate a mechanism whereby the migration of an optical property modifier away from a receptor (Sephadex beads in this example) is regulated by analyte. The details of the design of such a mechanism, such as the choice of modifier and receptor and concentrations for both, can vary from embodiment to embodiment, as can the slopes and positions of the curves in plots analogous to FIG. 4. FIG. 4 is given here as an example only and is not intended to be limiting.

Figure 5:
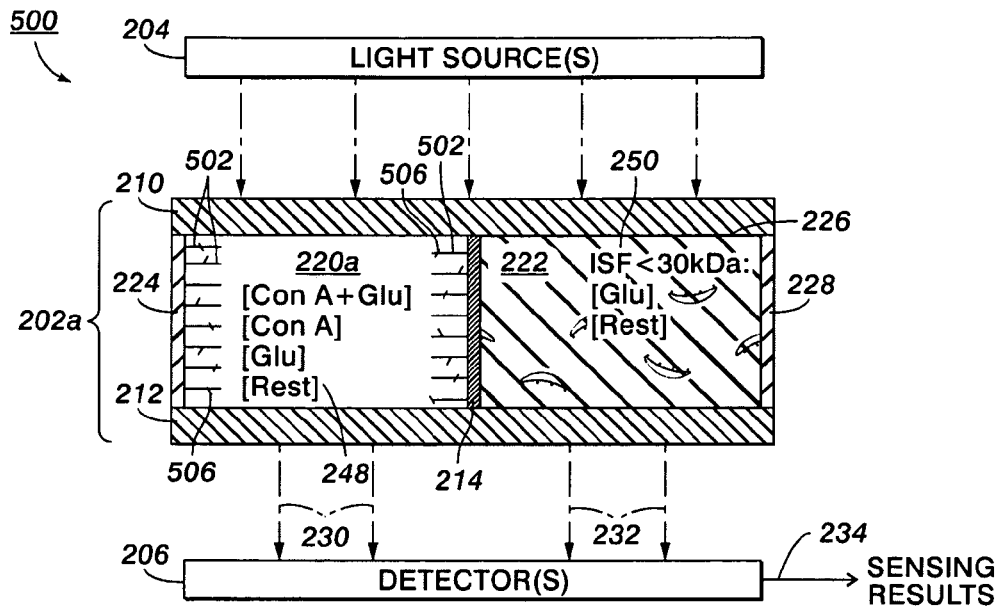
FIG. 5 is an alternative embodiment of the system of FIG. 2.

Turning to FIG. 5, illustrated is system 500, which is an alternative embodiment to the system of FIG. 2, including an optical cavity analyte detection component 202 a, wherein specificity container 220 a is configured with a reservoir comprising lamella (i.e., bookshelf-type structures) 502. The lamella have functionalized dextran (coated or otherwise attached to the lamella, and therefore also identified as 502 for convenience) to which Con A 506 binds. Similar to the operation in FIG. 2, as the glucose enters the specificity container, glucose releases the Con A from the receptor in the reservoir (i.e., the functionalized dextran of the lamella) by competitively binding to the Con A. The Con A-glucose complex [Con A+Glu] can then migrate into the optical cavity detection region 248, and the output detected by detectors 206 will then change in response. As the glucose concentration changes, the concentration of Con A-glucose complex changes; for example, upon a decrease in glucose concentration the concentration of Con A-glucose complex decreases and Con A-glucose diffuses back towards the lamella structures 502, wherein Con A rebinds with the dextran.

By the design of FIG. 5, the mesh and dextran beads of the previous embodiment are not necessary, and the reservoir includes the lamella structures.

Figure 6:
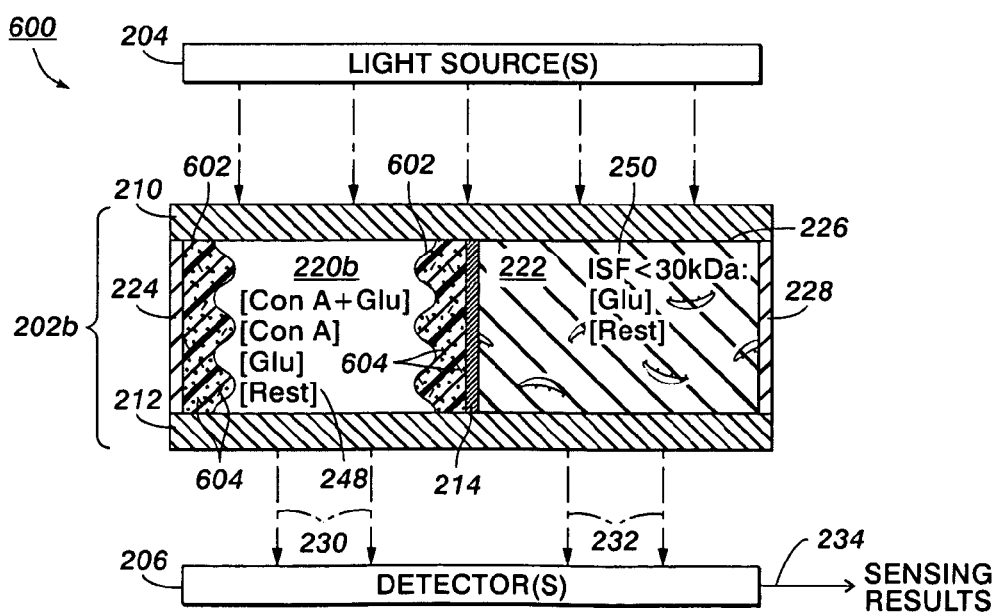
FIG. 6 is an alternative embodiment of the system of FIG. 2.

Turning to FIG. 6 shown is system 600, which is a further embodiment including an optical cavity analyte detection component 202b, with specificity container 220b of a system as illustrated in FIG. 2. In this design, reservoir includes foam or hydrogel components 602 functionalized by dextran (consisting of dextran, coated or otherwise attached to the foam or hydrogel and therefore also designated as 602 for convenience) having binding sites for Con A 604. Again, as the glucose moves (e.g., diffuses into the detector), it releases Con A bound to the dextran by competitively binding to the Con A, forming the Con A-glucose complex, which in turn diffuses into the detection region 248. In embodiments, the hydrogel can be a chemically or physically crosslinked hydrogel, including but not limited to crosslinked dextran. In embodiments, including embodiments in which the hydrogel material itself does not comprise dextran, dextran can be grafted or physically crosslinked to the hydrogel material by one of many means known in the art.

Figure 7:
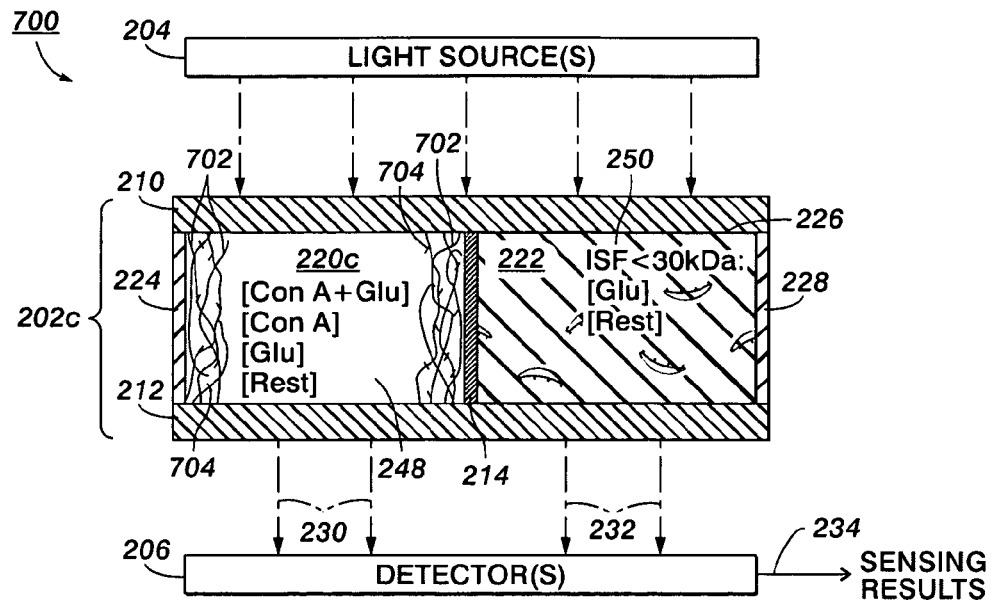
FIG. 7 is an alternative embodiment of the system of FIG. 2.

FIG. 7 illustrates a system 700, which is a further embodiment including an optical cavity analyte detection component 202c, with specificity container 220c of the system such as in FIG. 2, wherein the reservoir includes interwoven fibers 702 functionalized by dextran (coated or otherwise attached to the fibers and therefore also designated as 702 for convenience). In operation, Con A 704 is bound to the dextran to an extent determined by the concentration of glucose in the container 220. The introduction of the glucose again works in the manner previously described.

Figure 8:
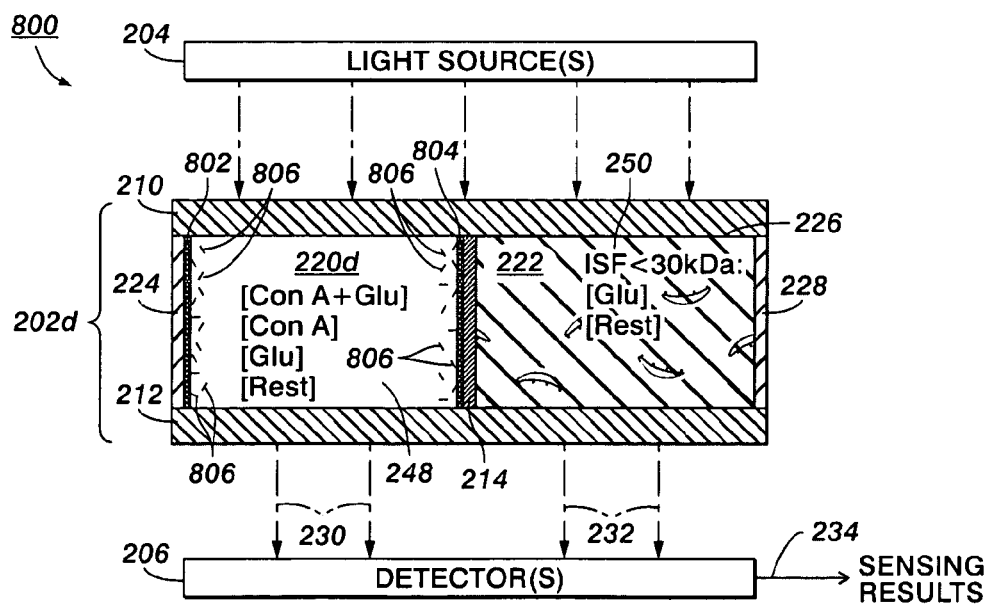
FIG. 8 is an alternative embodiment of the system of FIG. 2.

Depicted in FIG. 8 is a system 800, including an optical cavity analyte detection component 202d, wherein specificity container 202d, defines a reservoir as including the inner surface 802 of the MWCO membrane 224 and/or the inner surface 804 of wall 214, which have attached dextran (coated or otherwise attached to the inner surfaces and therefore also designated as 802, 804 for convenience). As in previous embodiments, the Con A 806 binds to the dextran with an affinity.

A particular aspect of the present application has to do with providing reservoirs which have a large amount of receptor binding sites. The foregoing discussion shows some embodiments of a reservoir used in various specificity container embodiments. It is to be understood however, there is a variety of arrangements which can meet the receptor requirements for particular implementations and the examples provided herein are not intended to be limiting to the overall idea of the application.

Figure 9:
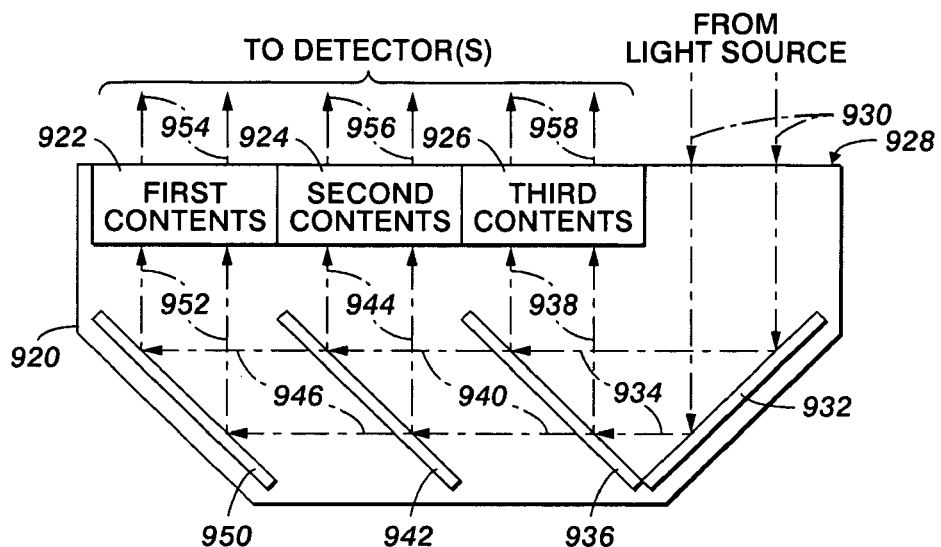
FIG. 9 is a schematic diagram of an implementation of an article with multiple containers that includes a reflection component.
Figure 10:
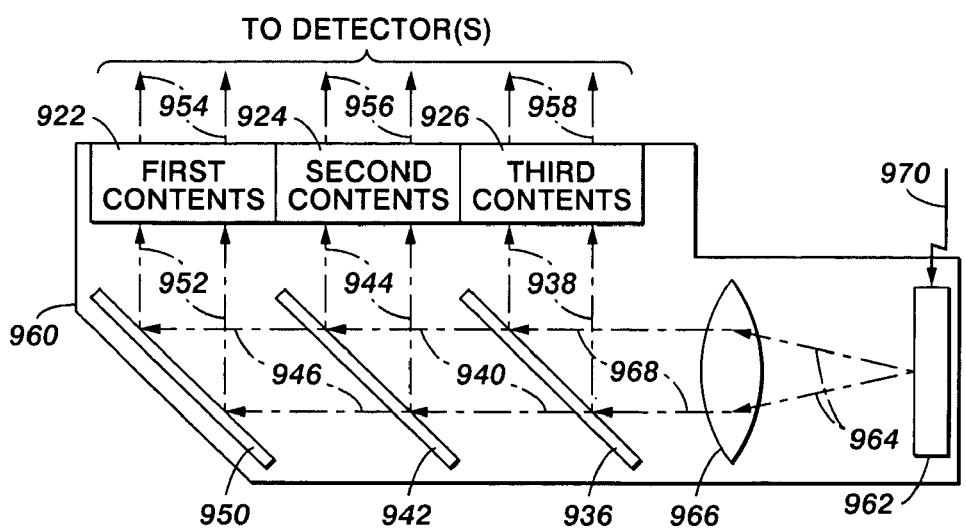
FIG. 10 is a schematic diagram of another implementation of an article with multiple containers that includes a reflection component and a light source.
Figure 11:
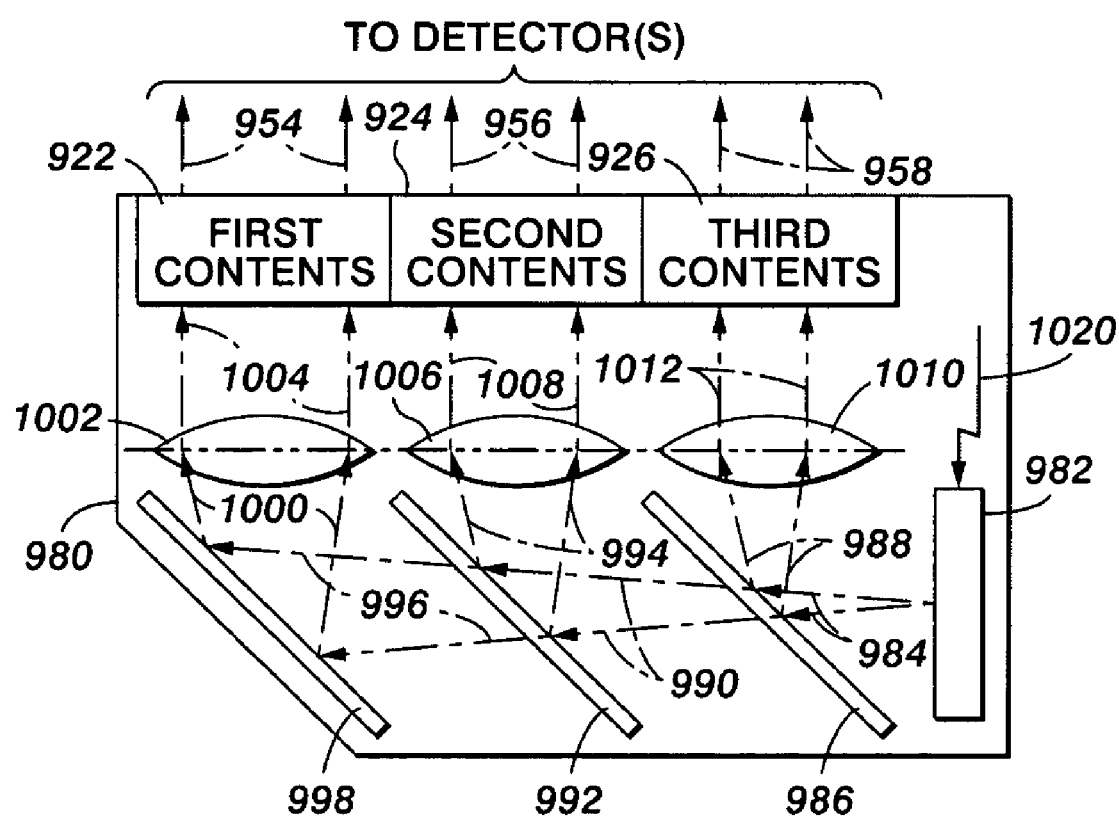
FIG. 11 is a schematic diagram of another implementation of an article with multiple containers that includes a reflection component and a light source.

FIGS. 9-11 illustrate approaches in which an implantable product with three containers includes a reflection component that divides incident light from a light source before providing it to the containers for operation as optical cavities that provide transmission mode output light. These techniques avoid the need for non-implanted light source and detector components on opposite sides of the implanted product when in a body part. The exemplary implementation of FIG. 9 receives light from outside the body part but on the same side as detectors, while those of FIGS. 10-11 include a narrow beam light source in the implanted product.

FIG. 9 depicts a configuration in which implantable product 920, which could be a passive device, includes containers 922, 924, and 926, at least one of which is specificity container and at least one of which is a non-specificity container. By "specificity container" it is meant that the container includes optical property modifier that migrates in a manner responsive to changes in concentration of an analyte with some degree of specificity for that analyte. A "non-specificity container" means a container that does not include optical property modifiers in an amount that would change an observed optical property to a significant degree. Product 920 also includes a reflection component with an incident light surface 928 through which incident light is received, said incident light represented by arrows 930.

Within the reflection component, mirror 932 receives the incident light in an incident light direction and provides input light, represented by arrows 934, in a different direction. Partially reflective mirror 936, such as with one-third reflectivity, receives the full intensity incident light and splits it, reflecting one-third intensity input light represented by arrows 938 in an entry direction to container 926, and transmitting two-thirds intensity light, represented by arrows 940. Partially reflective mirror 942, such as with one-half reflectivity, receives the two-third intensity light and splits it, reflecting one-third intensity input light represented by arrows 944 in an entry direction to container 924, and transmitting one-third intensity light, represented by arrows 946. Totally reflective mirror 950 receives the one-third intensity light and reflects it, providing one-third intensity input light represented by arrows 952 in an entry direction to container 922. In response, the optical cavities provide respective transmission mode output light, represented by arrows 954, 956, and 958 for photosensing, such as by appropriately positioned detectors that include discrete photosensors or a photosensing array.

FIG. 10 illustrates a configuration in which implantable product 960 includes parts similar to those of product 920 (FIG. 9), with counterpart parts that operate substantially the same way being labeled with the same reference numbers. In addition, product 960 includes narrow beam light source 962, such as a tunable VCSEL laser. The narrow beam from source 962, represented by arrows 964, might be somewhat divergent, and therefore passes through lens 966 or another appropriate optical collimating component, which provides a more collimated beam represented by arrows 968, if necessary. The collimated beam is then received by mirror 936, and so forth as described above in relation to FIG. 9.

Light source 962 can be controlled from outside a body part by control signals, represented by arrow 970. As a result, product 960 would require some sort of power source for light source 962.

FIG. 11 illustrates another configuration in which implantable product 980 includes some parts similar to those of products 920 (FIG. 9) and 960 (FIG. 10), with counterpart parts that operate substantially the same way being labeled with the same reference numbers. In addition, product 960 similarly includes narrow beam light source 982, such as a tunable VCSEL laser whose output beam does not diverge as rapidly as in FIG. 10. The narrow beam from source 982, represented by arrows 984, is divided before being collimated rather than after being collimated as in FIG. 10. The collimating techniques of FIGS. 10 and 11 could in principal be used together if advantageous, and more complex optical components capable of combining dividing and collimating operations could also be used.

Within the reflection component in FIG. 11, partially reflective mirror 986, such as with one-third reflectivity, receives the full intensity narrow beam and splits it, reflecting a one-third intensity narrow beam represented by arrows 988 in an entry direction to container 926, and transmitting a two-thirds intensity narrow beam, represented by arrows 990. Partially reflective mirror 992, such as with one-half reflectivity, receives the two-third intensity narrow beam and splits it, reflecting a one-third intensity narrow beam represented by arrows 994 in an entry direction to container 924, and transmitting a one-third intensity narrow beam, represented by arrows 996. Totally reflective mirror 998 receives the one-third intensity narrow beam and reflects it, providing a one-third intensity narrow beam represented by arrows 1000 in an entry direction to container 922. In general, any suitable combination of reflectivities for mirrors 986, 992 and 998 in FIG. 11, and 936, 942 and 950 in FIGS. 9 and 10 may be chosen.

Also within the reflection component, lens 1002 or another appropriate optical collimating component collimates the narrow beam from mirror 998, providing a collimated beam represented by arrows 1004 to container 922. Similarly, lenses 1006 and 1010 collimate the respective narrow beams from mirrors 992 and 986, providing collimated beams represented by arrows 1008 and 1012, respectively. In response, the optical cavities provide respective transmission mode output light as above.

As in FIG. 10, light source 982 can be controlled from outside a body part by control signals, represented by arrow 1020. As a result, product 980 would also require some sort of power source for light source 982.

Implementations as in FIGS. 9-11 could also be advantageous for reasons set forth above. In addition, they provide an elegant technique to increase the number of containers that can be operated as optical cavities, which are limited for some other configurations. Assuming suitable fluidic components for analyte, non-analyte, and reference containers, various suitable arrangements could be provided, including arrangements with more than three containers, and also more than three mirrors to provide their input light.

FIGS. 9-11 also show that the concepts described in this application may be used in conjunction with multiple containers (e.g., 4, 5, 6, 7, etc.). Additional particular implementations which may be achieved by use of three or more containers will be discussed. More particularly, in FIGS. 9-11, the first container 922 and the third container 926 are designed in accordance with the previous discussions. For example, container 922 is the specificity container of the various embodiments previously described, and may include Con A as an optical property modifier. Container 926 is similar to the second container (i.e., it has no Con A). These containers also include membranes to allow certain sized objects to flow into and out of the containers.

In using just two containers, the processes of releasing Con A and diffusion of Con A-glucose complex into the optical cavity detection region may introduce a time lag. To address this issue, a reference container (i.e., container 924) is added, which means it has been preloaded with a known solution and is sealed so other fluid, such as ISF, does not enter the interior.

Using this structure, it is possible to obtain a fast understanding of the direction a glucose concentration in ISF is moving i.e., whether the glucose concentration increasing or decreasing. For example, if container 926 (which does not have Con A) is changing compared to the reference container 924, it is possible to understand that there is a physiological change occurring. Then if the first container 922 (i.e., that with Con A) is moving in the same direction (for example, going up), then the fast change can be attributed to the glucose rising. Thus a time lag to determine a changing glucose is shortened. What has been described is different from obtaining a reading of the glucose value. However, in certain situations it may be valuable for a person to know there is a fast change occurring.

Another use for multiple container systems is to obtain a more refined reading. For example, container 922 may have a certain amount of Con A that can act as an optical property modifier, and container 926 may be provided with a much larger amount of Con A in the reservoir such that more Con A gets unbound from receptor for a given amount of glucose. Then container 926 would be read to ascertain very small changes in the glucose value. For example, this is understood that by using a larger amount of Con A, a more refined reading could be obtained, but due to the larger amount of Con A, the dynamic range of readings from container 926 alone would be reduced to a level that might not be suitable for diabetic patients, the dynamic range in the case being the change in concentration that would cause a shift of an intensity peak equal to the free spectral range. The measurement from container 922 would provide a less precise measurement of glucose concentration, but it provides enough precision that the range for the result to be deduced from container 926 data can be determined. Thus, the dynamic range of a combined measurement from containers 922 and 926 would be larger and still have the refinement of the measurement from container 926. Of course, in this embodiment, containers 922 and 926 would be designed as a specificity container, such as in the previous examples, i.e. they would include a reservoir and Con A modifier, and container 924 would be designed as a reference container. Thus, in this embodiment the measurement from a first container alone provides a less precise analyte concentration than the measurement from a second container alone, and the first container provides sufficient accuracy to deduce a more accurate measurement from the second container.

FIGS. 2 and 5-11 illustrate features of several exemplary implementations of products (or devices) and systems according to the concepts of the present application. In general, these embodiments incorporate containers, optical cavity detection regions, illumination sources (i.e., a light source such as a laser), and detectors (i.e., in the form of photosensors or other appropriate devices). However, the actual implantation of the components of the systems may be performed in a variety of arrangements and combinations. For example, the system could be implemented wherein the optical cavity structure is implanted and the illumination and detectors are external to the body. Alternatively, the illumination source and optical cavities could be implanted, and the detector remains external. Still further, it could be arranged where the optical cavity and detectors are implanted and the light source is external. Finally, each of the components, including the optical cavities, light source and detectors, may be implanted as a single unit.

When the light source is not implanted, the external light source may be brought near the exterior surface of the body, illuminating the optical cavities through the surface. Similarly, when the detector is not implanted, the signals coming out of the body are detected by a detector arrangement in close proximity thereto. Still further, when the light source and detector are external, they may, in one embodiment, have optical contact with the containers through optical fibers.

When the light source component is implanted within the body, it illuminates the optical cavity detection regions in response to receiving electromagnetic or other control signals supplied externally or upon internal triggers such as timing signals or power status of the internal power supply. If the detectors are not passive, and require energization, such external energization, as with the light source, may also be provided.

Still further, miniaturized power sources in the form of batteries, fuel cells, etc., may also be considered as possible means of energizing the required components.

In the foregoing examples, Con A has been described as being bound to dextran that is crosslinked (e.g., sephadex beads), immobilized, or otherwise contained in a reservoir region. However, it is to be appreciated that each of the above examples may be configured in an alternative form. In particular, the Con A can be immobilized within the reservoir and dextran added as an optical property modifier. Then the dextran would be bound to the immobilized Con A to a degree that depends on the concentration of glucose analyte. In such embodiments, when the glucose is then introduced and it binds to the Con A, it is the dextran that is released and moves into the detection region. For example, with attention to FIG. 5 in the lamella (i.e., bookshelf) embodiment of the specificity container, the Con A may be immobilized on the lamella, and the dextran then binds to the Con A. In this configuration, when the glucose concentration of the ISF increases and the glucose binds to the Con A, instead of the Con A being released, the dextran is released.

This embodiment has certain benefits as dextran is available over a large range of molecular weights, and dextran can be made much bigger than Con A by adding additional glucose links. Thereby the RI change due to a given amount of dextran being displaced from immobilized Con A at a given glucose concentration can be large compared with the RI change due to a given amount of Con A being displaced from immobilized dextran at the same glucose concentration. Also limited solubility and toxicity of Con A can be mitigated.

In foregoing examples, receptor binds reversibly with modifier within one or more reservoirs to provide a mechanism for regulating the migration of modifier in and out of an optical cavity detection region. In yet other embodiments, receptor binds reversibly with modifier in one or more optical cavity detection regions to provide a mechanism for regulating the migration of modifier in and out of the optical cavity detection region, the reservoir still being a region for storing modifiers that is separate from the optical cavity detection region. In these embodiments, the receptors are constrained in some manner to remain within the optical cavity detection region in order to prevent their migration into the reservoir. A system having such a mechanism responds to analyte as a result of changing ratio of "unbound" to bound modifier in the said optical detection region, "unbound" in this case meaning not bound to receptor, the "unbound" modifier being available to migrate, e.g. by diffusion, into and back out of the reservoir. The migration changes the amount of modifier in the detection region and therefore changes at least one optical property of the detection region.

Figure 12:
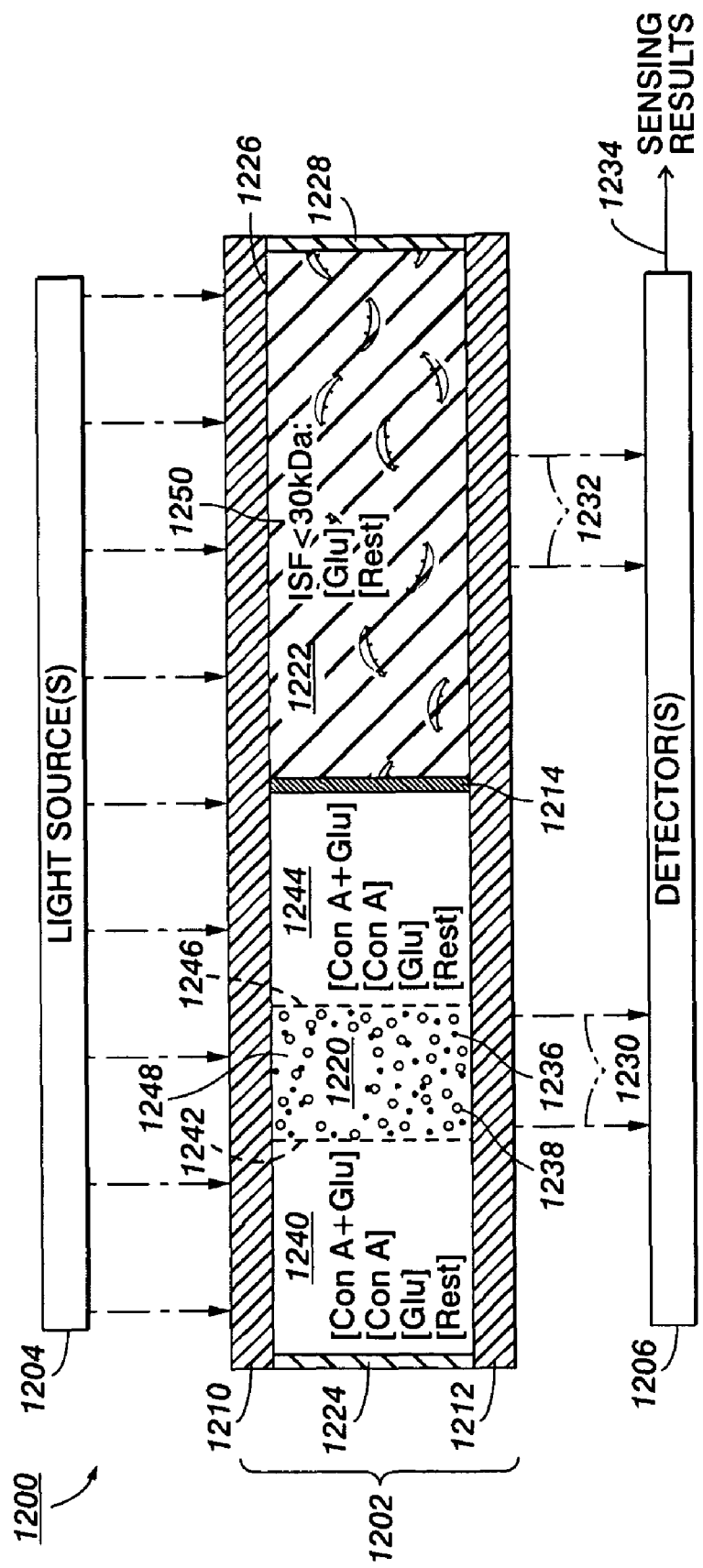
FIG. 12 is directed to another embodiment of the present application.

It is to be appreciated that examples of systems with receptors in optical cavity detection regions can be derived from examples with receptors in reservoirs. For example, illustrated in FIG. 12 is a system which incorporates the concepts of the present application as has been described above, including concepts to refine the transmission of the objects to be measured.

System 1200 illustratively includes optical cavity analyte detection component 1202, light source component 1204, and detector component 1206, with the implantable product including at least optical cavity component 1202, possibly in combination with one or more other optical cavity analyte detection components. The detector component 1206 may be one or a plurality of components (at times called detecting means) and may include but is not limited to photodetectors. Additionally, in one embodiment the illumination (light) source and detecting means may be placed in optical contact by use of optical fibers. Still further, in another embodiment the detecting means may be comprised of an RF signal from the system, which is received by an RF receiver.

Optical cavity analyte detection component 1202 could be an implementation of implantable product 10 in FIG. 1 in a long, narrow structure as described below in relation to exemplary implementations. A compact device with such a structure could be inserted in a minimally invasive manner in or under a human's skin to enable continuous detection of glucose without further invasive procedures.

In the illustrated example, optical cavity component 1202 is shown in cross-sectional view, illustrating how light-reflective components 1210 and 1212 and a set of wall parts including wall 1214 define containers 1220 and 1222 between light-reflective components 1210 and 1212, similar to FIG. 2. Each of containers 1220 and 1222 and bounding surfaces of components 1210 and 1212 can operate as a respective Fabry-Perot (FP) interferometer or etalon (also called an FP optical cavity), for example, with the objective of obtaining values indicating concentration of glucose in surrounding fluid. For example, indices of refraction of small samples from surrounding interstitial fluid can be measured, with each sample being contained within a FP optical cavity and the resulting output signal only being influenced substantially by changes within the sample.

As in FIG. 2, the cross section of FIG. 12 could be taken at a point along the length of the structure at which, when implanted under a human's skin, objects in interstitial fluid can transfer between the exterior and interior of each of first (or specificity) container 1220 and second container 1222 through respective filters described in more detail below. In each case, each container's respective filters are shown in its side wall disposed away from the other container, and could, for example, be mounted or otherwise attached to or connected in any suitable combination of one or more openings of any appropriate shape and size along the length of a container's side wall and/or in one or both of a container's end walls; these examples are merely illustrative, and filters could be mounted or otherwise attached to or connected in or through any appropriate part of the boundary (or boundary regions) of the container and in any appropriate way.

As in FIG. 2, container 1220 of FIG. 12 is bounded by reflective surfaces of components 1210 and 1212 and also by a surface of wall 1214; it can contain interstitial fluid filtered by filter 1224. Container 1222 is similarly bounded by reflective surfaces of components 1210 and 1212 and also by the opposite surface of wall 1214; it can contain interstitial fluid filtered by filter 1228. Container 1222 is shown with interstitial fluid filling its interior, except that any species larger than 30 kDa have been filtered out by filter 1228. However, for clarity of description, interstitial fluid is not illustrated in container 1220. Rather, such fluid and other objects in reservoir regions 1240 and 1244 are designated by identifiers [Con A+Glu], [Con A], [Glu] or [Rest], where [Rest] represents items of the interstitial fluid, filtered through filter 1224, other than glucose [Glu], [Con A] representing free Con A, and [Con A+Glu] representing a Con A-Glucose complex.

As in the example depicted in FIG. 2, each of filters 1224 and 1228 of FIG. 12 prevents a subset of objects in the ISF that can affect optical characteristics from being transferred into containers 1220 and 1222 at a relatively rapid rate. In some successful implementations, filters 1224 and 1228 have been implemented as macromolecule or molecular weight cut-off (MWCO) filters that effectively prevent molecules over an appropriate size such as about 15-30 kDa from entering containers 1220 and 1222, respectively. Filters 1224 and 1228 could be implemented in various other ways. As a result of filters 1224 and 1228, transfer of objects such as large molecules, cells, and so forth occurs only at a relatively slow, negligible rate or possibly does not occur at all if filters 1224 and 1228 are highly effective. In one embodiment the filters may be a dialysis membrane.

To achieve glucose specificity in RI measurements, all openings of the containers (cavity) are covered with an identical membrane, for example a membrane within the range of 10-100000 Da MWCO, more specifically a membrane with a 3-30 kDa MWCO, and even more specifically for exemplary purposes a membrane with a 15 kDa MWCO (i.e., filters 1224 1228 ). This prevents large molecules (e.g. Serum Albumin, Table 1) from entering the interior of the containers, while allowing small molecules (NaCl, Glucose etc.) to diffuse into them. Con A 1236 (Free Con A, Con A bound to dextran in the form of Sephadex beads 1238, or Con A bound to glucose) is/are located and kept inside the specificity container 1220 by use of the same membrane. Still further, in some embodiments the size of the filter may be approximately 1-6 nanometers, large enough to allow small molecules to pass while blocking large proteins, cells, and other large objects. Dextran beads are confined within the optical cavity detection region 1248 by a mesh (or reservoir filter) 1242.

From the ISF, molecules less than 15 kDa diffuse into both optical cavity detection regions 1248, 1250 of the containers 1220, 1222. The optical cavity detection region 1248 of the specificity container 1220 is partly filled with Sephadex beads (crosslinked dextran) 1238 which are inhibited from leaving the specificity container due to the use of the filters (e.g., container filter in the form of MWCO membranes). At the same time the beads also cannot enter the reservoir regions 1240 and 1244 of the specificity container 1220, because mesh (bead diameter >pore diameter) 1242, 1246 seals the optical cavity detection region 1248 from the reservoir regions 1240, 1244. Thus, the optical cavity detection region 1248 and the reservoir regions 1240, 1244 define separate areas of the specificity container 1220. Previous to being placed into the optical cavity detection region, the beads have been swollen in a suitable buffer (e.g. TRIS, PBS etc. at pH 7.4, buffer contains Ca and Mg salt) which also contained Con A. By this operation the Con A is bound to the beads. Thus the beads store the Con A. As mentioned above, Con A is released from the beads when glucose diffuses into the optical cavity detection region of the specificity container, as glucose competitively (with respect to dextran) binds to Con A. The resulting Con A-glucose complex, as well as any free Con A, can then diffuse through the mesh (where the pore diameter is greater than the Con A diameter) 1242, 1246 into the reservoir regions 1240 and 1244 of the specificity container.

The concentration of the released Con A-glucose complex is dependent on the free glucose concentration in the specificity container. This concentration also equilibrates with the free glucose concentration in the ISF so that the free glucose concentration within the container is not affected by the "glucose uptake" of Con A.

The RI difference between the two measurement regions in the two containers is comprised of the concentration difference of Con A (free and bound to glucose) in the specificity container versus no Con A in the reference container; this concentration difference is a measure for free glucose in the ISF. A straightforward procedure for correlating the RI difference to actual glucose values is to use a fluid with a known glucose value, and then the corresponding RI difference is identified as representing that glucose value. This process is repeated to obtain as many data points as necessary.

In one embodiment the use of the filter (MWCO) and mesh is not only to exclude objects that are larger than, for example, 15 kDa (depending on filter size) from the specificity container. Rather, they are also used to maintain the receptors and modifiers within the specificity container. For example, in the described glucose sensing application, it is the Con A which is maintained in the specificity container by use of the filters 1224.

As the Con A is much bigger than the glucose, combining them results in an amplification of the RI signal due to glucose alone of approximately 150 (i.e., approximately the ratio between the molecular weights of Con A and glucose).

To obtain a useful signal of this amplified RI change, the system is tuned by taking into account the amount of Con A put into the system, the binding affinity between the Con A and glucose, and the binding affinity between the Con A and the beads.

The amount of glucose which binds to Con A is correlated to the amount of glucose present in the ISF. Therefore the amount of release of Con A will be correlated to the amount of glucose in the system.

In operation, optical cavity detection region 1248 and 1250 receive input light from light source component 1204. Examples of light sources include one or more tunable lasers such as VCSELs, DFB lasers, DBR lasers, solid state lasers more generally, resonant cavity LED's, or other appropriate light sources as described above. In response, optical cavity component 1202 operates with two parallel optical cavity detection regions, each of which provides output light to detector component 1206, which has been successfully implemented with a separate photosensing detector for each cavity: One optical cavity detection region within container 1220 provides output light, represented by arrow 1230, with information about the contents of container 1220; the other optical cavity detection region within container 1222 provides output light, represented by arrow 1232, with information about the contents of container 1222. For example, if the optical cavities both operate as Fabry-Perot interferometers or etalons or as similar optical cavities with transmission or reflection modes, features of the modes of the two cavities will differ in a way that indicates difference of refractive index of contents of the respective containers. At the same time, the modes of the two cavities will be affected identically by some variations, such as variations in electrolyte concentration or in temperature, so that the spectral position difference between their modes will not be affected by such "common mode" variations. As a result, second container 1222 serves as a reference in the differential measurement, with variation in Con A-glucose complex concentration, and free Con A being the predominant cause of differences between spectral positions of the modes of the two cavities. In alternative embodiments, the intensity of light transmitted through the optical cavities is measured and the difference in absorption coefficients for the matter in the detection regions deduced. In yet other embodiments with birefringent modifiers, the polarization of light transmitted through the optical cavities is measured and the difference in birefringence properties of the two optical cavity detection regions is deduced. In Embodiments, the optical detection region of second container 1222 includes receptor and Con A to match the receptor and Con A in optical detection region 1248 to a significant extent.

In response to output light from the optical cavities, the photosensing detectors in detector component 1206 obtain sensing results that can include information about, for example, indices of refraction or absorption coefficients of contents of both containers, and the sensing results can be provided to an external component such as a CPU or other processor, as indicated by arrow 1234. The central processing unit (CPU) or other processor can use the sensing results to obtain information about glucose concentration, such as in one of the ways described below. It is important to note that correlation of the sensing results to glucose concentration does not necessarily require the actual deconvolution of a material property such as index of refraction or absorptivity from the sensing results. Rather, the important concept is that the optical property being measured, e.g. intensity or polarization of transmitted light, depends on the nature of the material in the optical cavity detection region and can therefore be correlated to changes in the material properties.

In a typical implementation, objects could be transferred into containers in component 1202 by diffusion or, if pumping or the like were implemented, by being carried by flow of bodily fluid, but if power is available in the implantable product for other operations as described below, electrochemical or electromechanical transport processes could also be implemented to manipulate flow of bodily fluid, such as to assure representative sampling or to extend the operational life of the implantable product, and such processes could also be controlled by a processor. Power could be available in many possible ways, including, for example, by inductive coupling, from one or more batteries, or from one or more photocells or other electromagnetic receivers.

Similar to the examples depicted in FIGS. 2 and 12, there are examples analogous to those depicted in FIGS. 5-8 in which receptor is contained in optical cavity detection regions rather than in reservoirs. The modifier still migrates between the detection regions and reservoirs, and the migration is still responsive to the concentration of analyte.

It is also to be noted that a dissociation constant is the chemical constant that defines the binding affinity between objects, such as between dextran and Con A or between glucose and Con A. It is known that a dissociation constant can be modified, for example by PEGylation of the Con A. PEGylation is a standard chemical process of covalent attachment of poly (ethylene glycol) polymer chains to another molecule. It is noted that solutions of unmodified Con A become turbid over time. PEGylation of Con A increases the solubility of Con A and the stability of Con A solutions over time. Use of PEGylated Con A provides certain intrinsic advantages such as it allows for tuning of the system for improved accuracy.

Openings into each container in a component of the devices described in FIGS. 1-2 and 5-12 can be shaped, sized, and located for the required update time constant and other constraints of the application; for example, for monitoring a homogeneous fluid for glucose, it may be desirable for objects to diffuse into containers having the greatest feasible volume. Since diffusion rate is proportional to area for a given filter structure, and since diffusion time affects accuracy of measurements, an objective is to maximize diffusion through the filter assemblies, such as by increasing their area so that they cover as much of the boundaries of analyte and non-analyte containers as possible. This can be achieved by providing filter-covered openings on all sides of the containers except the sides where light-reflective components bound optical cavities.

While the foregoing discussion has largely focused on detection by the use of measuring intensity of light transmitted through or reflected from optical cavity detection regions over a range of wavelengths, e.g. by noting shifts of intensity peaks, among other useful and identifiable optical properties, it is to be appreciated that optical property modifiers may also cause a change in the absorption spectrum that can be detected for the material in the detection regions. More particularly, the refractive index is detecting the shift between intensity outputs. However, signal information which includes the height, and more precisely the ratio between the maxima and minima of a signal output, also called the contrast in the signals, can be used as an optical property for determining analyte concentration and/or changes in concentration. Even though glucose does not absorb any significant amount of light in the wavelength range of 500-1000 nanometers, this process can be used because modifiers that have a different absorption spectrum than the analyte can be chosen.

The above discussion points out that the detection may occur in at least two different modes. Consider again the case of glucose analyte. First, the glucose may come into the system, and specifically bind with the Con A, and that will cause a distinct change in index of refraction observed as a spectral shift of intensity peaks, which again is used as the data for determining the glucose values. Alternatively, the glucose will again release the Con A, resulting in a change of absorption which can be measured as described above.

As mentioned, instead of determining optical properties that reflect the refractive index change in optical cavity detection regions, it is possible to measure the optical absorption in the detection region of the specificity container and still detect changes in the concentration of analyte in the fluid. U.S. application Ser. No. 11/702,329 explains in detail how this measurement is performed in a Fabry Perot etalon. The advantage of this measurement could be an enhanced sensitivity for the target molecule. The reasoning behind this idea is the fact that glucose, for example, does not have a significant absorption coefficient in the ultra violet (UV), visible (VIS) or near infrared (NIR) wavelength regions, and therefore could not be measured directly by measuring optical absorption. Con A on the other hand shows absorption in the UV-region (280 nm) and could be easily functionalized with a suitable absorber for other wavelengths (for example Con A functionalized with ATTO 565 is commercially available). This means that by changing the effective detection molecule (from glucose to Con A in our case) the absorption characteristics can be tailored. In particular this could allow for a specificity container that is specific to more than one target molecule by functionalizing more than one receptor with different absorbers in different wavelength regions. This would also require the use of different probing wavelengths which need to be sufficiently spectrally separated.

The foregoing discussion has primarily focused on the use of Con A, dextran, and glucose. However, it is to be appreciated the described receptor binding concepts are equally applicable to any other objects which have appropriate binding characteristics. Therefore, it is possible to generalize the described concepts to a receptor, an analyte, and an optical property modifier.

Thus, while the foregoing embodiments were focused on a CGM in ISF, the described measurement concepts could be extended to any other receptor-modifier arrangement or specific binding, that fulfills the criteria:

Reversible binding,

A degree of specificity of binding of analyte to either receptor or modifier,

Dissociation constant ($K_d$ value) of receptor-modifier binding allows for sufficient analyte binding to either receptor or modifier within an interesting detection concentration range of the analyte.

Optical property modifier (modifier for short) causes change of some observed optical property within the optical cavity detection region.

To illustrate a use of this generalized concept for a CGM detector, it is noted that in some instances a fluid may contain an "interfering compound" that alters the responsiveness of one or more containers to an analyte, meaning that an observed optical property of the optical cavity detection region at a given analyte concentration is different than it would be in the absence of the interfering compound. For example, a chosen receptor or modifier may bind to a small number of different "interfering compounds" present in the fluid in addition to the analyte, and bind with sufficient binding strength to cause unwanted interference with the detection of analyte. This problem can be solved by adding one or more additional specificity containers to the detector. Each of these specificity containers could include a different receptor or modifier that binds to an interfering compound and analyte with a different ratio of binding constants than the first specificity container.

As an example, consider the case where a first modifier binds to an analyte "A" and an interfering compound "I" with binding dissociation constants $K_{A1}$ and $K_{I1}$, respectively, with $K_{A1}<K_{I1}$. (A lower value of a binding dissociation constant corresponds to tighter binding.) The action of this first modifier in a first specificity container will be more sensitive to a given concentration of A than to the same concentration of I, giving it a favorable degree of specificity for A. However, depending on the ratio of the two dissociation constants and the possible concentrations for I, the uncertainty in the concentration of A due to possible binding of the first modifier with I may be large enough to cause an undesirably large uncertainty in the detection of the analyte. Adding an additional container with a modifier that binds to A and I with binding dissociation constants $K_{A2}$ and $K_{I2}$ having a different ratio than $K_{A1}/K_{I1}$ provides a means for deconvolving the contributions of analyte A and interfering compound I to the signal from the first specificity container, thereby reducing the uncertainty in the detected concentration of A. (The extreme case of $K_{A2}$ approaching infinity is one such case.) For any given signal from the first specificity container, the possible values of [A] and [I] consistent with the signal will lie on a curve in a graph with coordinate axes of [A] and [I], [A] and [I] being the concentrations of A and I, respectively. Likewise, the possible values of [A] and [I] consistent with the signal from the said additional container will lie on a separate curve. The two curves will intersect at the actual values of [A] and [I]. It is to be appreciated that the deconvolution of [A] and [I] can be done even if the specificity of the first container for A is low relative to the interfering compound, i.e. $K_{A1}>K_{I1}$. Preferably, though, a first modifier will be found for which $K_{A1}<K_{I1}$, and a second modifier will be found for which $K_{A2}>K_{I2}$. Also, it is to be appreciated that the problem of an interfering compound interfering with the binding of analyte to receptor, rather than to modifier, can be addressed similarly. Thus in one embodiment the detected optical property of the first region and the detected optical property of the second region is used to separate the effect of the analyte on the detected optical property of the first region from the effect of the compound other than the analyte, on the detected optical property of the second region, the compound being an interfering compound.

As an example of an interfering compound, maltose and glucose bind to ConA with comparable binding strengths. Consequently a chamber with the ConA modifier or receptor cannot distinguish well enough different concentrations of glucose and maltose if there is some reason that maltose may be present at a high concentration, e.g. as a result of intravenous injection of a solution having a high concentration of maltose. A different receptor such as maltose-binding protein (MBP) has a higher binding strength to maltose (lower binding dissociation constant) than glucose. For example, the wild type MBP from E. coli binds maltose with a dissociation constant near 1 µM, but does not exhibit high affinity binding to D-glucose. Furthermore, affinity of MBP for maltose can be adjusted by introducing one or more mutations. While an engineered variant of the E. coli protein with a mutation of the aspartate at position 95 to cysteine does not show an altered affinity for maltose, when an additional mutation is introduced by replacing the tryptophan at position 340 with alanine, the affinity of MBP for maltose is decreased from 1.4 µm to 2.8 mM. Furthermore MBP reversibly binds to amylose resin or crosslinked amylose and can be eluted from the resin by addition of maltose. Therefore, amylose or crosslinked amylose may operate as a receptor with MBP modifier in a maltose specificity container for the interfering compound maltose. In other embodiments, amylose may operate as a modifier and immobilized MBP as a receptor.

Illustrating one of the above embodiments in more detail, a specificity container specific for maltose detection can be made with MBP as the optical property modifier, or "modifier" for short, amylose as the receptor, and maltose as the interfering compound. The receptor binds to the modifier. The interfering compound, when present in the sample, causes dissociation of the receptor-modifier complex in a manner dependent on the concentration of interfering compound, increasing the concentration of MBP that can migrate into the optical cavity detection region. Any subsequent decrease in maltose concentration will result in increased binding of the amylose receptor to the MBP modifier, reducing the concentration of modifier in the optical cavity detection region. Samples containing other compounds, such as glucose analyte, which have a low affinity for the receptor, would not be as effective at releasing the receptor from the modifier.

A modified form of MBP can be used to allow for improved measurement of the concentration of the interfering compound maltose in some ranges of concentration. For example, the use of an MBP variant with an affinity for maltose of 2.8 mM would allow for detection of maltose that is sensitive in the millimolar range, which would be suitable to distinguish between glucose and maltose in a CGM utilizing Con A in a second specificity container.

It has to be appreciated that the concept of detecting MBP by changes in an optical property of an optical cavity detection region only requires an additional specificity container (specificity container 2) as described previously. This additional chamber does not only enable a compensation for an undesired interfering compound (e.g. maltose) in the specificity chamber for glucose (specificity container 1), but it also provides additional information from the sensor, namely the maltose concentration. Thus, in embodiments the maltose may be both an analyte and an interfering compound.

This concept of incorporating specificity for more than one analyte can be extended to any desired number of objects in this device. For example an assay for lactic acid could be included by adding a container that has a receptor for a reversible binding reaction with lactic acid and a competing modifier. Of course, for these extended concepts as well as the maltose example, the releasable binding concepts discussed above would also be employed in these embodiments to extend the usefulness of an implanted and/or inserted device.

Continuing the concept of generating the foregoing discussions to receptors, modifiers, analytes, and interfering compounds, it is to be understood that previously introduced concepts may also be described in a more generalized manner. For example, the receptors could be bound to the membranes and walls of the etalon (i.e., the containers), providing additional binding sites for the receptors and/or allow omitting storage medium (i.e. beads), if the required surface density of binding sites in an embodiment allows for it. In this case, a mesh in the proposed embodiments is obsolete as well.

The receptor could be bound permanently within the storage region. The competitive binding would then release the modifier (for example, in the Con A-glucose case with immobilized Con A the modifier would be the dextran) which provides optical property-signal specificity and, in some embodiments, amplification.

Thus, while the foregoing embodiments were focused on a CGM in ISF, the described measurement concepts could be extended to any other receptor-modifier arrangement or specific binding, that fulfills the criteria:

The modifier reversibly binds to the receptor,
The modifier changes one or more optical properties of the optical cavity detection region sufficiently.

A conformational change of the modifier upon binding with the analyte could be used, if this results in a change in an optical property of the modifier. No reservoir containing a receptor would then be necessary.

The properties of the receptor may be modified to achieve suitable dissociation constants, diffusion times, RI changes and solubilities.

It will be appreciated that various of the above-disclosed and other features and functions, or alternatives thereof, may be desirably combined into many other different systems or applications. Also, it will be appreciated that various presently unforeseen or unanticipated alternatives, modifications, variations or improvements therein may be subsequently made by those skilled in the art, which are also intended to be encompassed by the following claims.

The invention claimed is:

1. A method for detecting concentration of an analyte in a fluid, the method comprising:
   providing a reflective optical cavity system having two or more light-transmissive regions at least partially bounded by components having light-transmissive and light-reflective properties, at least two of the components having substantially parallel surfaces;
   detecting an optical property of a first region of the two or more regions in the system, the first region located in a container having a reservoir for one or more modifiers of one or more optical properties of the first region, the movement of said one or more modifiers being responsive to changes in concentration of said analyte;
   detecting an optical property of a second region of the two or more regions in the system, the second region located in a container having a reservoir for one or more modifiers of one or more optical properties of the second region; the movement of said one or more modifiers being responsive to changes in concentration of a compound other than said analyte in the fluid;
   using said detected optical property of the first region and said detected optical property of the second region to separate the effect of said analyte on said detected optical property of the first region from the effect of said compound other than said analyte, said compound being an interfering compound; and
   determining the concentration of the analyte based on the difference in the effect of the analyte and the effect of the compound other than the analyte.

2. A method according to claim 1 wherein one or more optical property detected is the intensity of light transmitted through or reflected from an optical cavity detection region and further including determining the shift in the spectral position of one or more intensity peak.

3. A method according to claim 2 further including determining the shift in the spectral position of one or more intensity peak divided by the free spectral range.

4. A method according to claim 1 further including determining changes in refractive index in the first and second containers of a system with a first container in which the first region is located and a second container in which the second region is located.

5. A method according to claim 1 further including determining changes in optical absorbance in the first and second containers of a system with a first container in which the first region is located and a second container in which the second region is located.

6. A method according to claim 4 further including determining a concentration of the first analyte by the determined refractive index.

7. A method according to claim 5 further including determining a concentration of the first analyte by the determined absorption.

8. A method according to claim 1 further including, detecting an optical property of an optical cavity detection region in at least a third container which is preloaded with a known reference fluid, the preloaded third container being sealed so the fluid external to the third container cannot enter the interior of the third container, the third container being a reference container.

9. A method according to claim 1 further including implanting the first and second containers which are physically connected in or underneath the skin in contact with interstitial fluid.

10. A method according to claim 1 further including illuminating the first and second containers with an operatively associated illumination source.

11. A method according to claim 1 further including providing one or more illumination sources, and a detecting means for measuring one or more properties of the first and second containers.

12. A method according to claim 11 further including implanting or partially implanting the first and second containers, in or underneath the skin in contact with interstitial fluid, and wherein the detecting means is not implanted.

13. A method for detecting concentration of an analyte in a fluid, the method comprising:
    providing a reflective optical cavity system having two or more light-transmissive regions at least partially bounded by components having light-transmissive and light-reflective properties, at least two of the components having substantially parallel surfaces;
    detecting an optical property of a first optical cavity detection region of the two or more optical cavity detection regions in the system, the first optical cavity detection region located in a container having a reservoir for one or more modifiers of one or more optical properties of said region, the movement of said one or more modifiers between said reservoir and said first optical cavity detection region being responsive to changes in concentration of said analyte;
    detecting an optical property of a second optical cavity detection region of the two or more optical cavity detection regions in the system, the second optical cavity detection region located in a second container;
    using the difference in the optical property detected from the first optical cavity detection region and the optical property detected from the second optical cavity detection region to determine the concentration of the analyte in said fluid.

14. A method according to claim 13 wherein one or more optical property detected is the intensity of light transmitted through or reflected from an optical cavity detection region, and further including determining the shift in the spectral position of one or more intensity peak divided by the free spectral range.

15. A method according to claim 13 further including implanting or partially implanting the first and second containers in or underneath the skin in contact with interstitial fluid.

16. A method according to claim 13 further including inputting light into the first and second containers with an operatively associated illumination source.

17. A method according to claim 13 wherein the reservoir contains a receptor.

18. A method according to claim 13 wherein the said first optical cavity detection region contains a receptor.

19. A method according to claim 17 wherein analyte is glucose, the modifier comprises dextran, and the receptor comprises a protein having at least one binding site for glucose and dextran.

20. A method according to claim 17 wherein analyte is glucose, the receptor comprises dextran, and the modifier comprises a protein having at least one binding site for glucose and dextran.

21. A method according to claim 17 wherein the analyte is one of urea, insulin, lactate, ions, therapeutic drugs or immunosuppressant drugs, and the receptor is one of lectin, concanavalin A, Fab fragments, hormone receptors, drug receptors, aptamers or molecularly-imprinted polymers.

22. A method according to claim 18 wherein analyte is glucose, the modifier comprises dextran, and the receptor comprises a protein having at least one binding site for glucose and dextran.

23. A method according to claim 18 wherein analyte is glucose, the receptor comprises dextran, and the modifier comprises a protein having at least one binding site for glucose and dextran.

24. A method according to claim 18 wherein the analyte is one of urea, insulin, lactate, ions, therapeutic drugs or immunosuppressant drugs, and the receptor is one of lectin, concanavalin A, Fab fragments, hormone receptors, drug receptors, aptamers or molecularly-imprinted polymers.

25. A method according to claim 13 further including,
detecting an optical property of an optical cavity detection region in a third container preloaded with a known reference fluid, the preloaded third container being sealed so the fluid external to the third container cannot enter the interior of the third container, the third container being a reference container.

26. A method according to claim 13 further comprising:
detecting one or more optical properties of one or more additional optical cavity detection regions in the system, the one or more additional optical cavity detection regions located in corresponding one or more additional containers, each container having a reservoir for one or more modifiers of one or more optical properties, the movement of said one or more modifiers being responsive to changes in concentration of a compound in the fluid; and
determining the concentration of a compound using detected optical properties.

27. A method according to claim 26 wherein the said compound is an interfering compound that alters the responsiveness of the one or more containers to one or more analytes.

28. A method according to claim 27 wherein one of the one or more analytes is glucose, a modifier in the first container comprises dextran, a receptor in the first container comprises a protein having at least one binding site for the glucose and dextran, and the interfering compound is maltose.

29. A method according to claim 27 wherein one of the one or more analytes is glucose, a modifier in the first container comprises a protein having at least one binding site for the glucose and dextran, a receptor in the first container comprises dextran, and the interfering compound is maltose.

30. A method according to claim 13 further including implanting or partially implanting the first and second containers, in or underneath the skin in contact with interstitial fluid, and wherein the detecting means is not implanted.

31. A method according to claim 13 wherein the optical property of at least one of the optical cavity detection regions is the intensity or polarization of light transmitted through or reflected from the optical cavity detection region.

32. A method according to claim 13 wherein the optical property of at least one of the optical cavity detection regions is the intensity of light transmitted through or reflected from the optical cavity detection region over a range of wavelengths.

33. A method according to claim 1 further comprising the step of generating a radiofrequency from the detected optical property of the first region and the second region of the system and monitoring said radiofrequency signals generated by the system, using a radiofrequency receiver.

34. A method according to claim 13 further comprising the step of generating a radiofrequency from the detected optical property of the first region and the second region of the system and monitoring said radiofrequency signals generated by the system, using a radiofrequency receiver.

* * * * *